US008648078B2

(12) United States Patent
Zampieri et al.

(10) Patent No.: US 8,648,078 B2
(45) Date of Patent: *Feb. 11, 2014

(54) PLK INHIBITOR SALTS

(75) Inventors: Massimo Zampieri, Cesano Maderno (IT); Italo Beria, Nerviano (IT); Annalisa Airoldi, Nosate (IT); Ilaria Candiani, Busto Arsizio (IT); Riccardo Frigerio, Sovico (IT)

(73) Assignee: Nerviano Medical Sciences S.R.L., Nerviano (MI) (IT)

( * ) Notice: Subject to any disclaimer, the term of this patent is extended or adjusted under 35 U.S.C. 154(b) by 0 days.

This patent is subject to a terminal disclaimer.

(21) Appl. No.: 13/387,051

(22) PCT Filed: Jul. 22, 2010

(86) PCT No.: PCT/EP2010/060659
§ 371 (c)(1),
(2), (4) Date: Mar. 12, 2012

(87) PCT Pub. No.: WO2011/012534
PCT Pub. Date: Feb. 3, 2011

(65) Prior Publication Data
US 2012/0157468 A1      Jun. 21, 2012

(30) Foreign Application Priority Data
Jul. 29, 2009   (EP) .................................... 09166760

(51) Int. Cl.
*A61K 31/497* (2006.01)
*C07D 491/00* (2006.01)
(52) U.S. Cl.
USPC ......................................... 514/252; 544/251
(58) Field of Classification Search
USPC ..................... 514/252.16; 544/251
See application file for complete search history.

(56) References Cited

U.S. PATENT DOCUMENTS 4,582,831 A * 4/1986 Robertson .................. 514/226.5

FOREIGN PATENT DOCUMENTS

WO   WO 2008074788 A1 *   6/2008
WO   WO 2008/074788 A1    11/2010

OTHER PUBLICATIONS

Kumar, L, et al. "Salt Selection in Drug Development." PharmTech. com. Mar. 2, 2008.*
Sheth, A.R., et al. "Relationship between the Structure and Properties of Pharmaceutical Crystals." KONA. No. 23 (2005), pp. 36-48.*
Bastin, R.J., et al. "Salt Selection and Optimisation Procedures for Pharmaceutical New Chemical Entities." Organic Process Research & Development. (2000), 4, pp. 427-435.*
International Search Report dated Nov. 16, 2010 issued in PCT/EP2010/060659.

* cited by examiner

*Primary Examiner* — Andrew D Kosar
*Assistant Examiner* — John S Kenyon
(74) *Attorney, Agent, or Firm* — Scully, Scott, Murphy & Presser, P.C.

(57) ABSTRACT

The present invention relates to novel crystalline, water-soluble salts of a plk inhibitor. Such crystal salts are for example L-tartrate, succinate, phosphate, mesylate, maleate, L-malate, hydrochloride, fumarate (half mole of counterion), fumarate, citrate (half mole of counterion), benzenesulfonate and L-aspartate (half mole of counterion). New crystal forms of the base as well as solvates and hydrates of such new salt forms, a process for their preparation, their utility in therapy and to the pharmaceutical compositions containing them are also claimed and described in the present application.

7 Claims, 16 Drawing Sheets

PLK INHIBITOR SALTS

The present invention relates to novel crystalline, water-soluble salts of a plk inhibitor, to a process for their preparation, to hydrates, solvates and polymorphs of such new salt forms, to their utility in therapy and to pharmaceutical compositions containing them.

Cancers are a leading cause of death in humans; surgery, radiation and chemotherapy are the useful means to fight cancers.

PLK1 is a serine threonine kinase essential for proper mitotic progression.

Expression of PLK1 is seen in all proliferating normal tissues while overexpression is observed in a series of tumors including breast, prostate, ovary, lung, gastric and colon cancers. Upon PLK1 depletion in cancer cell by RNAi, inhibition of proliferation and decreased viability resulting in cell-cycle arrest with 4 N DNA content followed by apoptosis is observed. Although four different PLKs family members are described in humans, the inhibition of the enzymatic activity or the depletion of PLK1 is sufficient to induce G2/M cell cycle block and apoptosis in tumor cell lines and tumor regression in xenograft models. In addition, for the other PLKs, a tumor suppressor function has been described and PLK2 and PLK3—but not PLK1—are reported to be expressed in non-proliferating, differentiated post mitotic cells, like neurons, indicating a possible better safety profile for a PLK1 specific compound (see for instance: Strebhardt K, et al., Nat Rev Cancer 2006; 6(4):321-30)

The use of mitotic inhibitors in cancer therapy is a widely accepted clinical strategy for the treatment of a broad range of human cancers (see for instance: Jackson J R, et al., Nature Reviews Cancer 2007; 7, 107-117). Taxanes (paclitaxel and docetaxel) and vinca alkaloids (vincristine and vinblastine) work by either stabilizing or destabilizing microtubules with catastrophic consequences in cells progressing through mitosis. They are first line therapeutics for several tumor types including Hodgkin's disease, non-Hodgkin's lymphoma, testicular cancer, neuroblastoma and Wilms' tumor (vinca alkaloids) and second line in cisplatin-refractory ovarian, breast, lung and esophagus cancers (Taxanes). However, due to the role of microtubules in processes such as cell migration, phagocytosis and axonal transport certain toxicities such as peripheral neuropathy are frequently observed with these agents.

Pyrazoloquinazolines described and claimed in the patent application WO2008074788 (Nerviano Medical Sciences Srl.) are potent inhibitors of PLK1 and are thus useful in the treatment of proliferative disorders, especially cancer.

The compound 937 having the following formula:

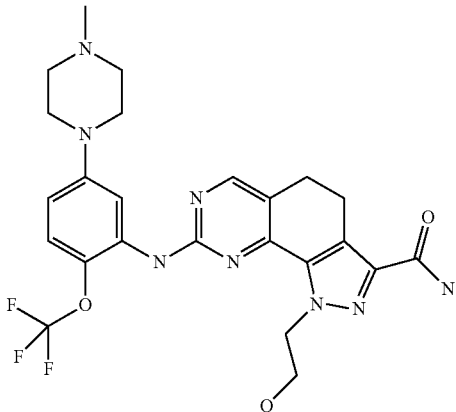 [SMILES: CN1CCN(c2ccc(OC(F)(F)F)c(Nc3ncc4c(n3)-c3c(c(C(N)=O)nn3CCO)CC4)c2)CC1]

is one of the compounds described and claimed in the above noted patent application. Also its preparation, pharmaceutical compositions comprising it and medical uses are described and claimed there.

The compound 937 is 1-(2-hydroxy-ethyl)-8-[5-(4-methyl-piperazin-1-yl)-2-trifluoromethoxy-phenylamino]-4,5-dihydro-1H-pyrazolo[4,3-h]quinazoline-3-carboxamide and its preferred preparations are described in examples 38 and 40 in the above noted patent application.

The compound 937 is a crystalline poorly water-soluble compound, which shows aqueous solubility of less than 0.1 mg/ml.

The solubility of the compound 937 is about 4 mg/ml in 10% polysorbate 80 in 5% dextrose solution, about 7 mg/ml in aqueous 50% polyethylene glycol 400 in 5% dextrose solution and about 8÷9 mg/ml when formulated as hydrochloride or mesylate in situ salt. The compound 937 was also suitable for aqueous methocel suspensions in the approximate range of 2÷8 mg/ml.

The obtained free base was initially formulated as in situ salt or methocel suspension in order to allow administration during early pharmacological and toxicological evaluation. Though solving the problem of the early formulation approach, the applied formulation approaches were not suitable for development of an oral formulation.

Preclinical investigation of an active pharmaceutical ingredient requires the possibility of dissolving it in a suitable vehicle. Usually the objective is to render the compound water-soluble in order to be suitable for preparation of injectable sterile formulations; fast dissolution of the drug substance contained in solid dosage forms such as hard gelatin capsules and immediate-release tablets also requires adequate water-solubility.

The observed poor solubility of compound 937 makes it difficult to formulate and administer.

Furthermore, the free base is slightly hygroscopic since showing a maximum uptake of about 1% of water at 90% relative humidity (RH) at 25° C.

Moisture uptake is also a significant concern for pharmaceutical powders. Moisture has been shown to have a significant impact, for example, on the physical, chemical and manufacturing properties of drugs, excipients and formulations. It is also a key factor in taking decisions related to packaging, storage, handling and shelf life and successful development requires a sound understanding of hygroscopic properties.

For instance, conversion from an anhydrous to a hydrate form may be observed when the relative humidity exceeds a critical level and moisture content rapidly increases in the solid. This has not only an impact on the physical and pharmaceutical properties of the drug per se, but also on its biopharmaceutical perspective. Moreover, it is well known, that hydrate forms usually tends to be less soluble with respect to a homologous anhydrous form, with potential detrimental effect also on the dissolution rate properties of the active compound per se and on its absorption profile through the gastrointestinal tract. At the same manner, conversion from a crystalline to an amorphous form may be observed in presence of humidity, with potential disadvantages in terms of physical stability. The amorphous active drug substance, if deliquescent, can for instance absorb relatively large amounts of water from the atmosphere up to its dissolution while also its chemical stability can be affected since the amorphous structure, being thermodynamically activated, is more prone to chemical degradation and to chemical interaction with other chemical species. Thus the performance and the efficacy of both formulation and active ingredient may be significantly changed.

In addition, the powder bulk density of the free base is low, being of about 90 mg/ml.

Favorable bulk properties, such as powder bulk density, is also desirable. Higher powder bulk density relates to a more suitable particle morphology, allows improved flowability and results in improved properties of a pharmaceutical composition. Higher powder density allows, for example, a more suitable capsule formulation manufacturing process or a higher dosage strength within similar capsule size with the concrete possibility of reducing number and/or size of the capsules to be administered, specially during the early clinical phase.

Accordingly, there is a need in therapy of a water-soluble salt of the compound 937 endowed with good and reproducible physicochemical and bulk properties, such as adequate solubility, low hygroscopicity, crystallinity and favorable powder bulk density but also solid state and chemical stability at variable storage temperature, humidity and illumination conditions, ensuring proper biopharmaceutical behavior and allowing a safer and efficacious oral administration.

As it is well known by the skilled person, salt formation does not always result in an enhancement of solubility characteristics (see for instance: Shozo Miyazaki, et al., International Journal of Pharmaceutics 1980; 6(1), 77-85) as well as the behavior of the different salts in terms of solubility and/or dissolution and/or sensitivity to counter-ion effect can be different according to the properties of each drug-counterion couple.

Surprisingly, the present inventors have solved the above-described technical problem by providing novel salts as well as novel crystalline forms of salts of the compound 937 having improved physicochemical and bulk properties.

In fact, the novel salts are crystalline, rapidly-dissolving solids with high water solubility; moreover these salts are low or moderately hygroscopic, thus substantially introducing important advantages in handling, storage and formulations etc; finally, these salts have a powder bulk density surprisingly greater than that of the freebase, in addition to possessing all the other advantages, in particular therapeutic advantages, exhibited by the free base when formulated as in situ salt or methocel suspension.

Surprisingly, new salt forms of the compound 937 were found and proven to be crystalline as well as the free base. The property of being crystalline powders renders these forms particularly suitable for pharmaceutical development.

BRIEF DESCRIPTION OF THE DRAWINGS

The invention is also illustrated by reference to the accompanying drawings described below.

The thermogram reports temperature (° C.) on the x axis while heat flow (mW) is reported on the y axis.

Figure 10:
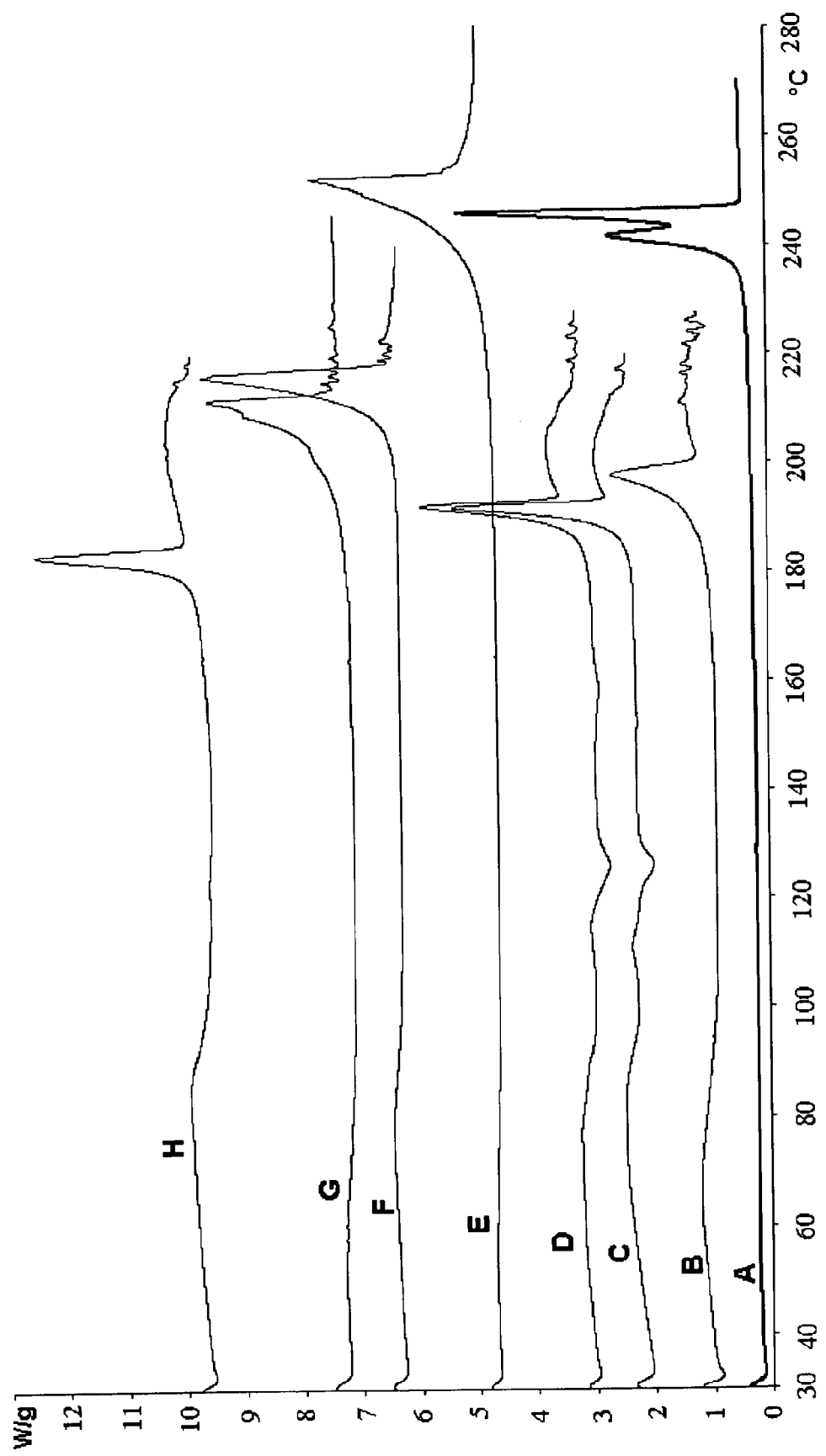

FIG. 10 shows the DSC thermograms of compound 937 free base form I (A1), free base form II (A2), L-tartrate salt form I (B), succinate salt form II (C-D), fumarate salt form I (E), maleate salt form I (F), maleate salt form II (G) and L-malate form I (H).

Figure 11:
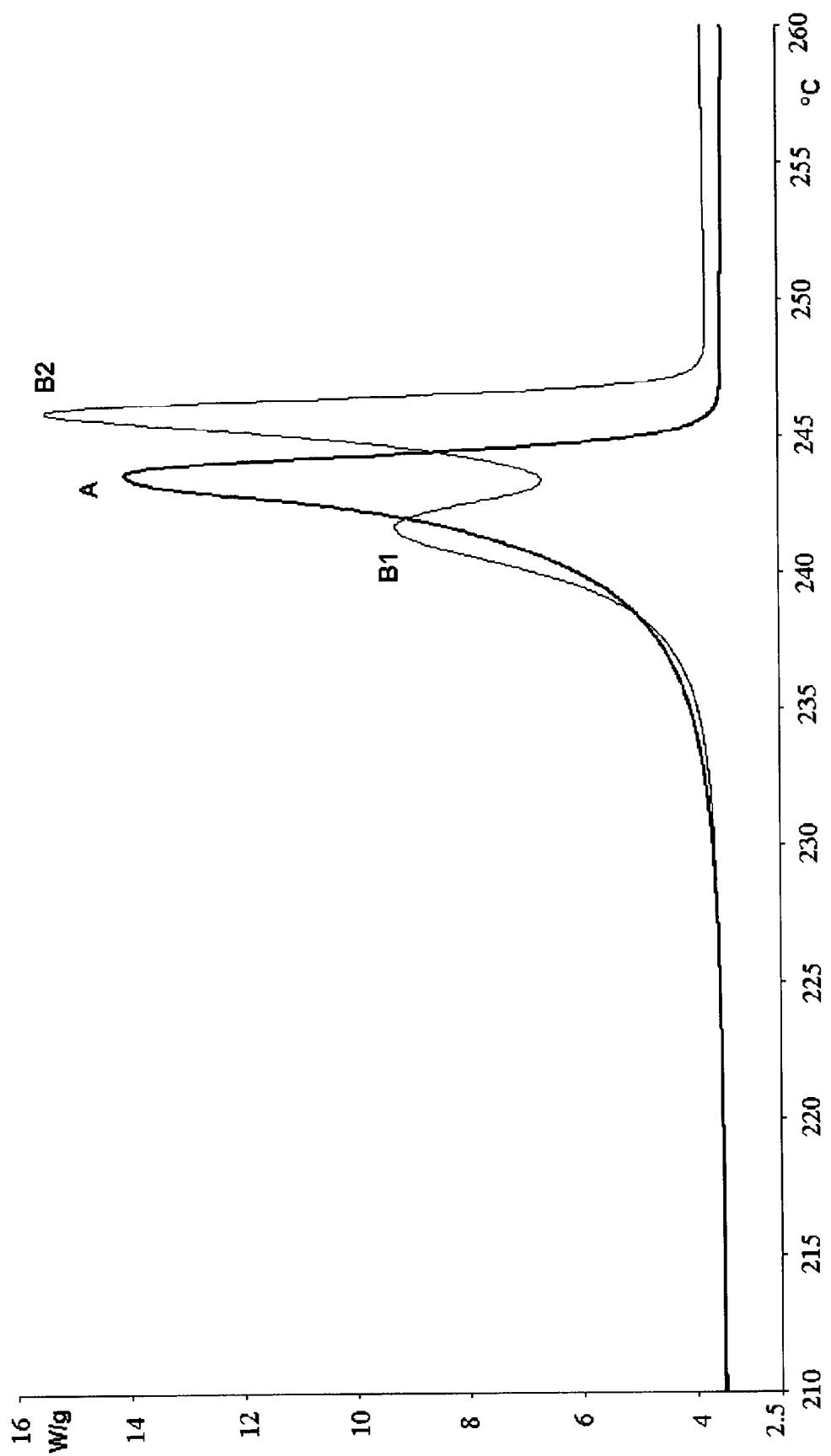

FIG. 11 shows details of the DSC thermograms of compound 937 free base form I (A-B1) and free base form II (B2).

Figure 12:
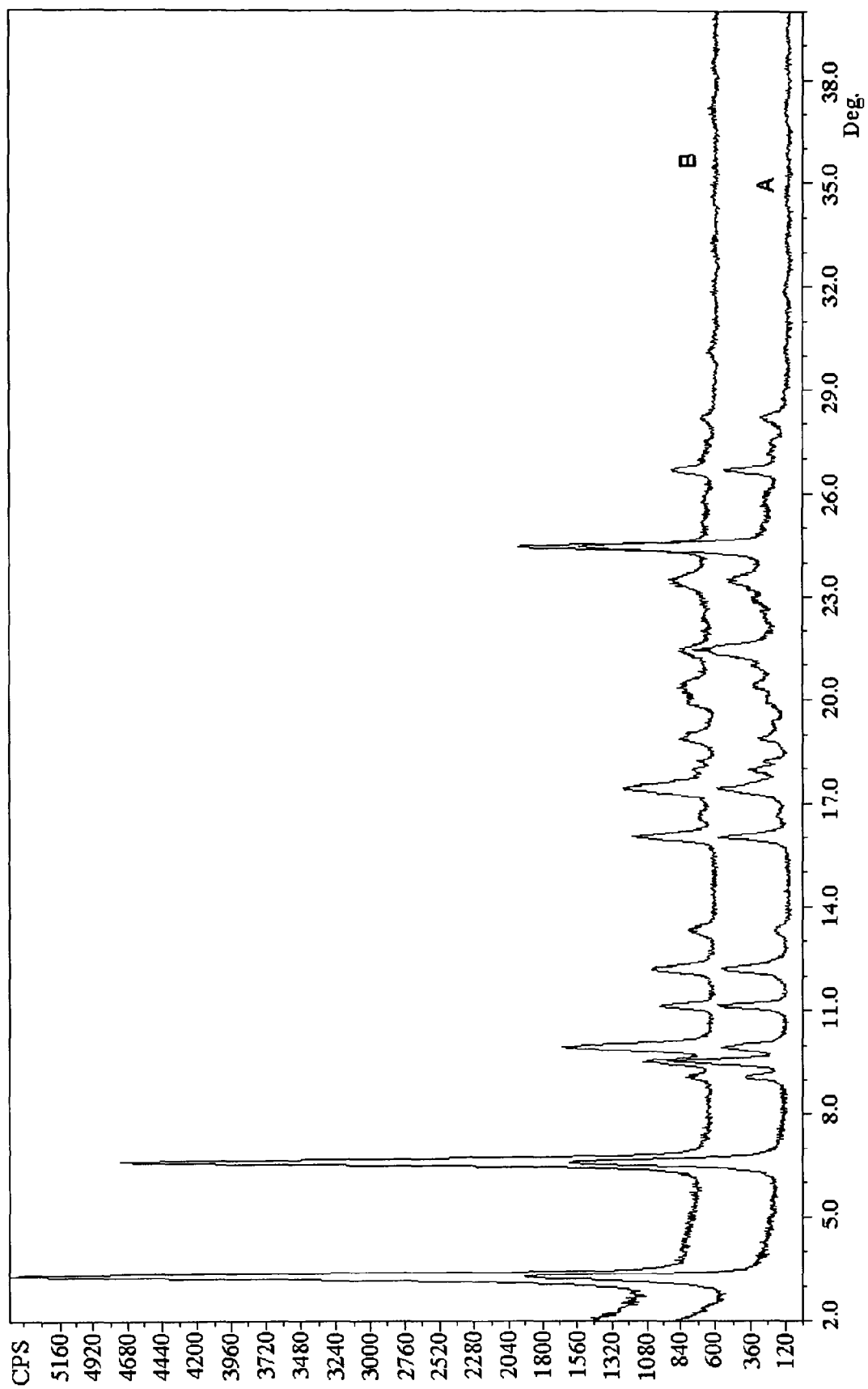

FIG. 12 shows the X-ray diffractograms of the batches of compound 937 freebase form I (A-B) also characterized by the DSC profiles reported in FIG. 11.

Figure 13:
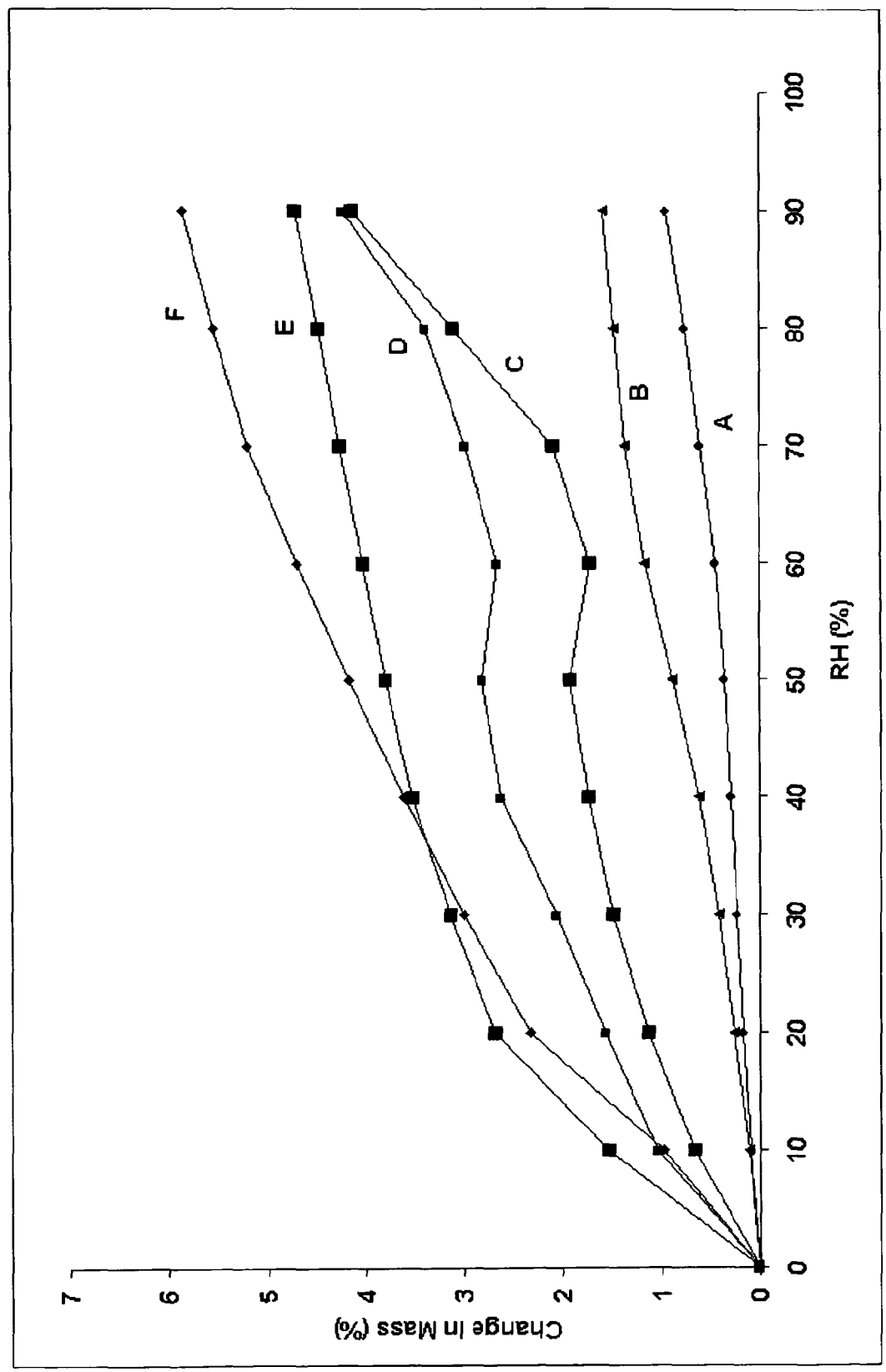

FIG. 13 shows the DVS profiles (hygroscopicity test) of compound 937 free base form I (A), fumarate salt form I (B), maleate salt form II (C), succinate salt form II (D), L-malate salt form I (E), L-tartrate salt form I (F).

Figure 14:
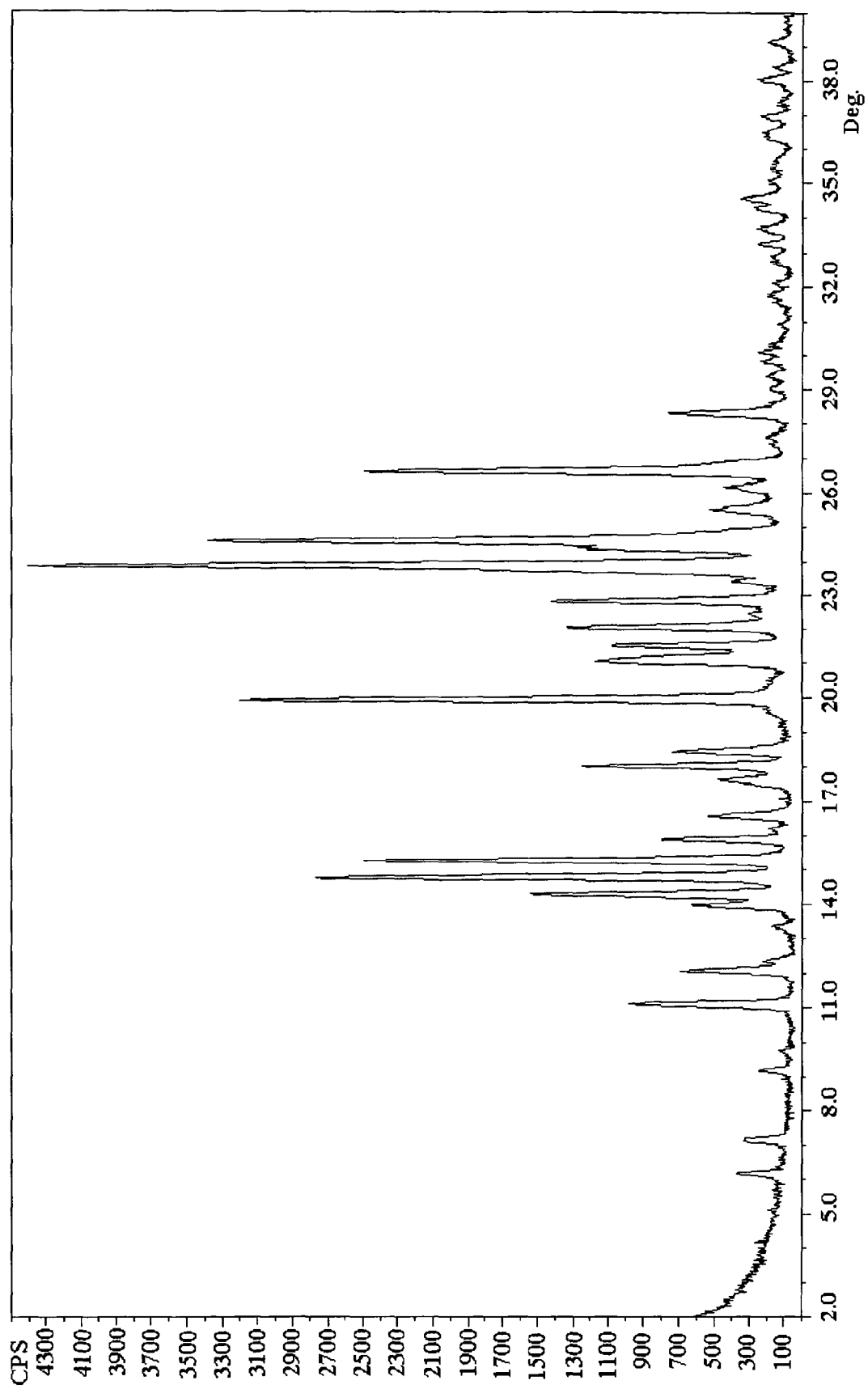

FIG. 14 shows the X-ray diffractogram of a scaled-up batch of the of compound 937 fumarate salt form I.

Figure 15:
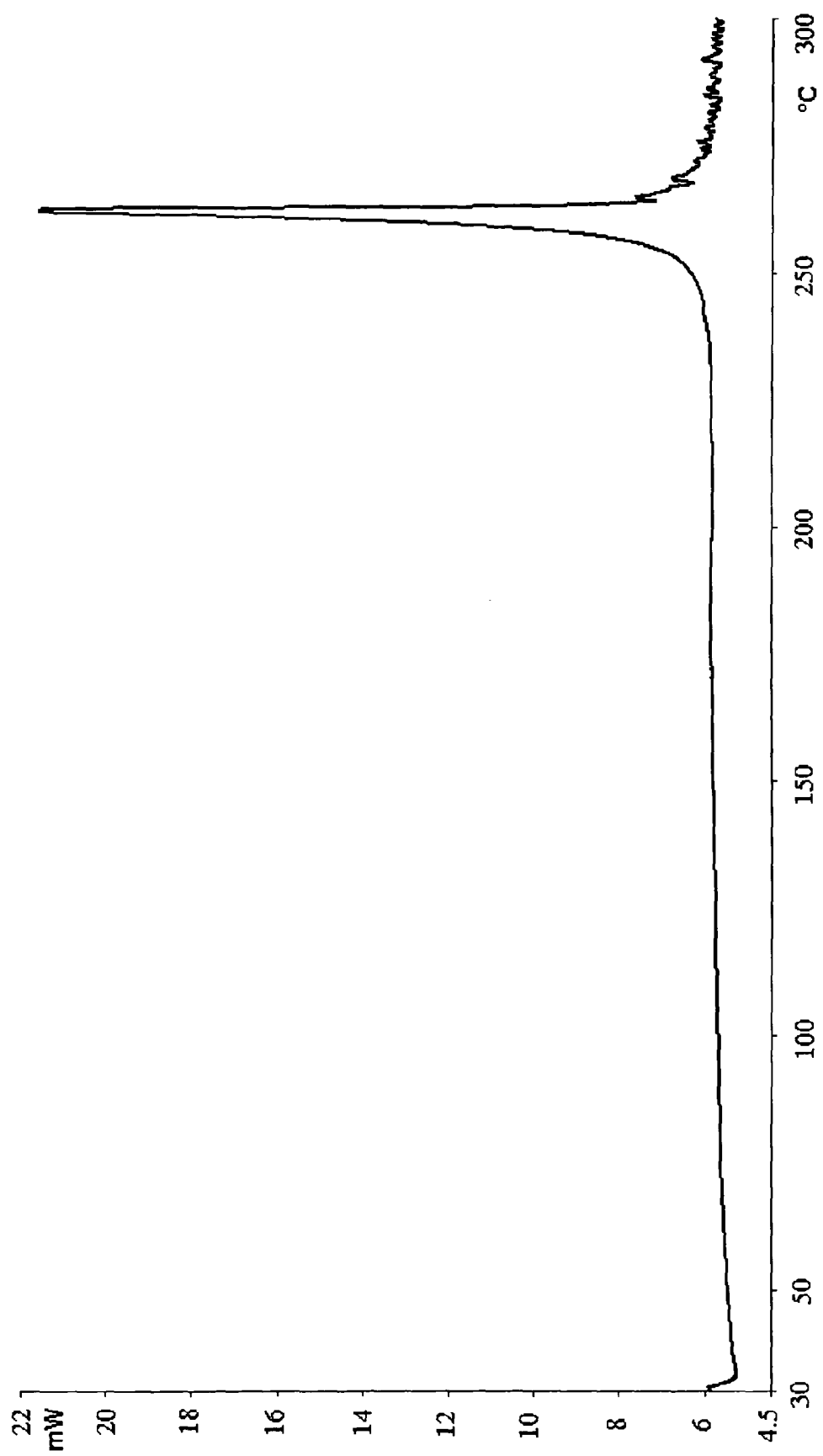

FIG. 15 shows the DSC profile of a scaled-up batch of the of compound 937 fumarate salt form I.

Figure 16:
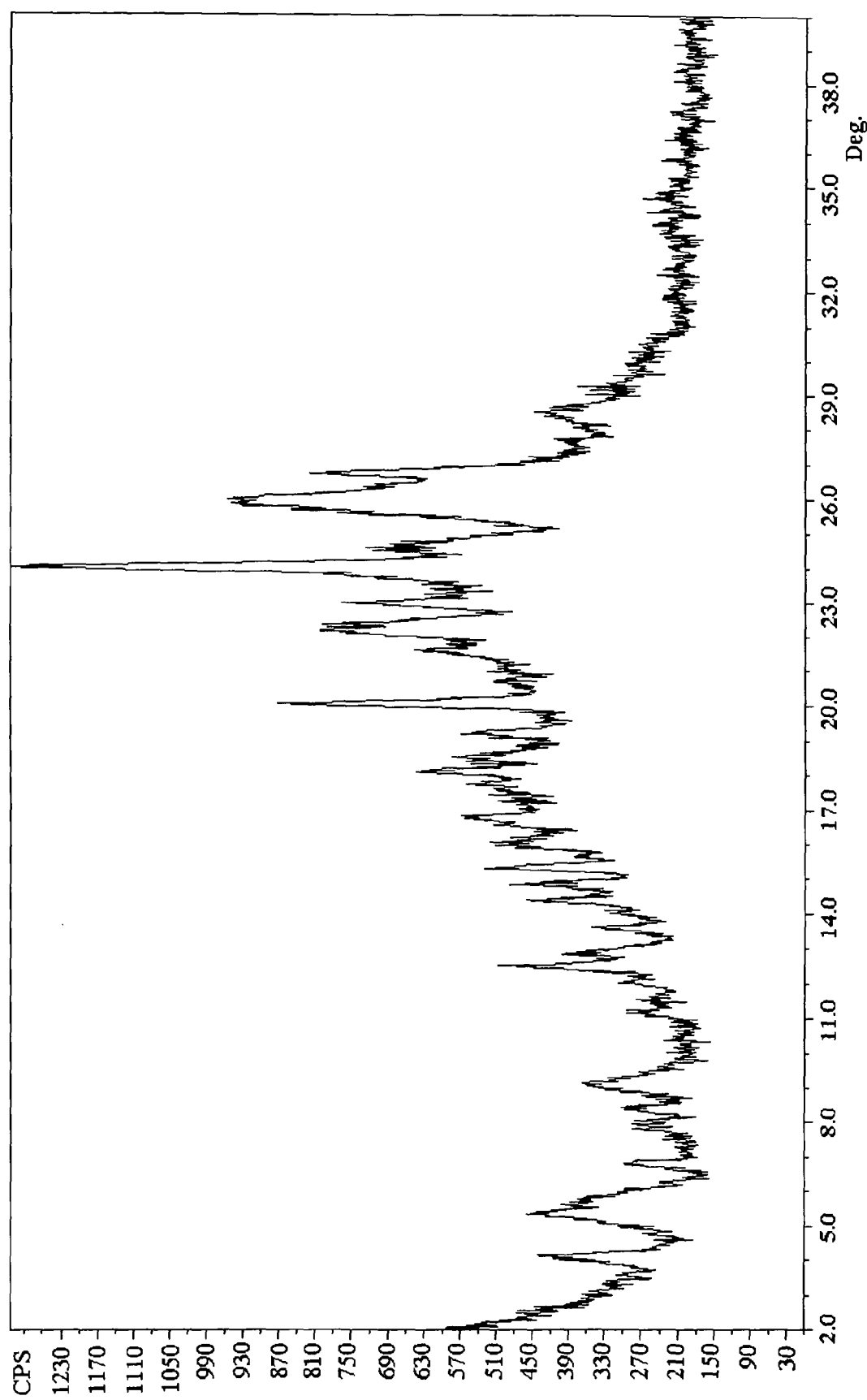

FIG. 16 shows the X-ray diffractogram of a scaled-up batch of the of compound 937 fumarate salt form II.

In a first aspect, the present invention relates to new salts of compound 937 selected from L-tartrate, succinate, phosphate, mesylate, maleate, L-malate, hydrochloride, fumarate (half mole of counterion), fumarate, citrate (half mole of counterion), benzenesulfonate and L-aspartate (half mole of counterion), and their crystalline forms, solvates and hydrates.

In particular the present invention relates to new salts of compound 937 selected from L-tartrate, succinate, maleate, L-malate and fumarate, and their crystalline forms, solvates and hydrates.

More particularly the present invention relates to new salts of compound 937 selected from L-tartrate, L-malate and fumarate, and their crystalline forms, solvates and hydrates.

Further more particularly the present invention relates to new crystalline forms of compound 937 fumarate salt, and its solvates and hydrates.

Most particularly the present invention relates to the solvates of compound 937 fumarate salt.

Such salts of compound 937 can be obtained by known analogy methods by means of the desired stoichiometric addition of solvent or aqueous solutions of the counterion to the free base dissolved in a suitable solvent. Such solvent is preferably an organic, in particular anhydrous, solvent chosen preferably from methanol, ethanol, dichloromethane and their mixtures. If necessary, the precipitation or the crystallization of the obtained salt may be favored by addition or reworking in an anhydrous apolar solvent, for instance diethylether, n-hexane or cyclohexane.

According to the present invention, the definition of salts also comprises their crystalline forms, solvates and hydrates thereof.

The term "solvates" as used herein, means compounds formed by solvation, for example as a combination of solvent molecules with molecules or ions of a solute. Well known solvent molecules include water, alcohols and other polar organic solvents. Alcohols include methanol, ethanol, n-propanol, isopropanol, n-butanol, isobutanol, and t-butanol. Alcohols also include polymerized alcohols such as polyalkylene glycols (e.g. polyethylene glycol, polypropylene glycol).

The term "hydrates" as used herein, means compounds formed by solvation, wherein the solvent is water.

Unless otherwise specified, when referring to "solvates" and "hydrates" the present invention includes both stoichiometric and non-stoichiometric ones.

Stoichiometric solvates have a fixed ratio of solvent molecules to the molecules of the compound. This is typically due to a bonding interaction between the solvent and the compound molecule. In non-stoichiometric solvates, the solvent is not present in a fixed ratio to the molecules of the compound and often can vary. In a non-stoichiometric solvate, the solvent is often present in the void spaces or channels within the crystalline lattice. Stoichiometric hydrates have a fixed ratio of water molecules to the molecules of the compound. This is typically due to a bonding interaction between the water and the compound molecule. In non-stoichiometric hydrates, the water is not present in a fixed ratio to the molecules of the compound and often can vary. In a non-stoichiometric hydrate, the water is often present in the void spaces or channels within the crystalline lattice.

Then, in a further aspect, the present invention relates to the new stable crystalline forms of the compound 937 as free base.

A further object of the invention is to provide a pharmaceutical composition comprising any salt of the compound 937 as above defined, a crystalline form, solvate or hydrate of the compound 937 fumarate salt or a crystalline form of the compound 937 as free base as active ingredient and a pharmaceutically acceptable excipient and/or carrier.

A further object of the invention is to provide any salt of the compound 937 as above defined, a crystalline form, solvate or hydrate of the compound 937 fumarate salt, or a crystalline form of the compound 937 as free base for the use as a medicament.

A further object of the invention is to provide any salt of the compound 937 as above defined, a crystalline form, solvate or hydrate of the compound 937 fumarate salt, or a crystalline form of the compound 937 as free base, either alone or in association with other therapeutic agents, for use in treating a mammal, comprising a human being, suffering from a disease state treatable by PLK inhibition.

Additionally, the present invention relates to any salt of the compound 937 as above defined, a crystalline form, solvate or hydrate of the compound 937 fumarate salt, or a crystalline form of the compound 937 as free base, for use in treating a mammal, comprising a human being, suffering from a disease state treatable by PLK inhibition, such as cell proliferative disorders, viral infections, autoimmune and neurodegenerative disorders.

Additionally, the present invention relates to any salt of the compound 937 as above defined, a crystalline form, solvate or hydrate of the compound 937 fumarate salt, or a crystalline form of the compound 937 as free base, for use in treating a mammal, comprising a human being, suffering from a disease state treatable by PLK inhibition, characterized in that the cell proliferative disorder is cancer.

A further object of the invention is to provide a method for treating a mammal, including a human being, in need of PLK inhibition comprising administering to said mammal a therapeutically effective amount of any salt of the compound 937 as above defined, a crystalline form, solvate or hydrate of the compound 937 fumarate salt, or a crystalline form of the compound 937 as free base.

Finally, another object of the invention is to provide use of any salt of compound 937 as above defined, a crystalline form, solvate or hydrate of the compound 937 fumarate salt, or a crystalline form of the compound 937 as free base, either alone or in association with other therapeutic agents, for the manufacture of a medicament for the treatment of a disease state treatable by PLK inhibition.

The term "disease state treatable" means that the treatment according to the invention provides remission of the disease state or at least the conditions and quality of life of the mammal under treatment are improved.

Examples of such disease states are in particular different cancers that may include carcinoma such as bladder, breast, colon, kidney, liver, lung, including small cell lung cancer, esophagus, gall-bladder, ovary, pancreas, stomach, cervix, thyroid, prostate, and skin, including squamous cell carcinoma; hematopoietic tumors of lymphoid lineage including leukaemia, acute lymphocitic leukaemia, acute lymphoblastic leukaemia, B-cell lymphoma, T-cell-lymphoma, Hodgkin's lymphoma, non-Hodgkin's lymphoma, hairy cell lymphoma and Burkett's lymphoma; hematopoietic tumors of myeloid lineage, including acute and chronic myelogenous leukemias, myelodysplastic syndrome and promyelocytic leukaemia; tumors of mesenchymal origin, including fibrosarcoma and rhabdomyosarcoma; tumors of the central and peripheral nervous system, including astrocytoma, neuroblastoma, glioma and schwannomas; other tumors, including melanoma, seminoma, teratocarcinoma, osteosarcoma, xeroderma pigmentosum, keratoxanthoma, thyroid follicular cancer and Kaposi's sarcoma. Examples of such disease states are also specific cellular proliferation disorders such as, for example, benign prostate hyperplasia, familial adenomatosis polyposis, neurofibromatosis, psoriasis, vascular smooth cell proliferation associated with atherosclerosis, pulmonary fibrosis, arthritis, glomerulonephritis and post-surgical stenosis and restenosis.

The effective dose of compound 937 salts may vary according to the disease, severity of the disorder and the conditions of the patient to be treated. Therefore the physician, as always, must set the optimal dose for each patient. Anyway, the effective dosage range may be from about 5 to about 500 mg per dose (calculated as a free base), from 1 to 5 times daily.

A salt of the compound 937 as above defined, a crystalline form, solvate or hydrate of the compound 937 fumarate salt, or a crystalline form of the compound 937 as free base, is readily orally absorbed, therefore it is preferably orally administered.

Needless to say, the compounds of the present invention may be administered by any administration route, for instance by parenteral, topical, rectal and nasal route.

As a further aspect it has been found that compound 937 fumarate salt can be obtained as a crystalline solid in a crystalline form named form I. Form I is a high melting crystalline form of compound 937 fumarate salt that shows a moderate water uptake of 1.6% at 25° C./90% RH that is reversible by lowering RH at constant temperature of 25° C. (PXRD profile: FIG. 1J; DSC profile: FIG. 9J; DVS profiles: FIG. 13B and Table 11—other references about PXRD and DSC profiles are described in table 1)

It has been found that compound 937 fumarate salt can be obtained as a crystalline solid also in stoichiometric ratio of 0.5:1. (PXRD profile: FIG. 1I; DSC profile: FIG. 9I).

Compound 937 fumarate salt can be obtained as a crystalline solid in a crystalline form named form II (PXRD profile: FIG. 16).

As a further aspect it has been found that compound 937 L-malate salt and compound 937 L-tartrate salt can be obtained as a crystalline solid in crystalline forms both named form I. Compound 937 L-malate salt and compound 937 L-tartrate salt are moderately hygroscopic, both showing respectively a water uptakes of about 4.7% and 5.8% at 25° C./90% RH. The water content is rather stable at room conditions thus the two salts can be considered stable hydrates (PXRD profiles: L-malate FIG. 1G, L-tartrate FIG. 1B; DSC profiles L-malate FIG. 9G, L-tartrate FIG. 9B; DVS profiles: L-malate FIG. 13E, L-tartrate FIG. 13F; other references about PXRD and DSC profiles are described in table 1).

Figure 6:
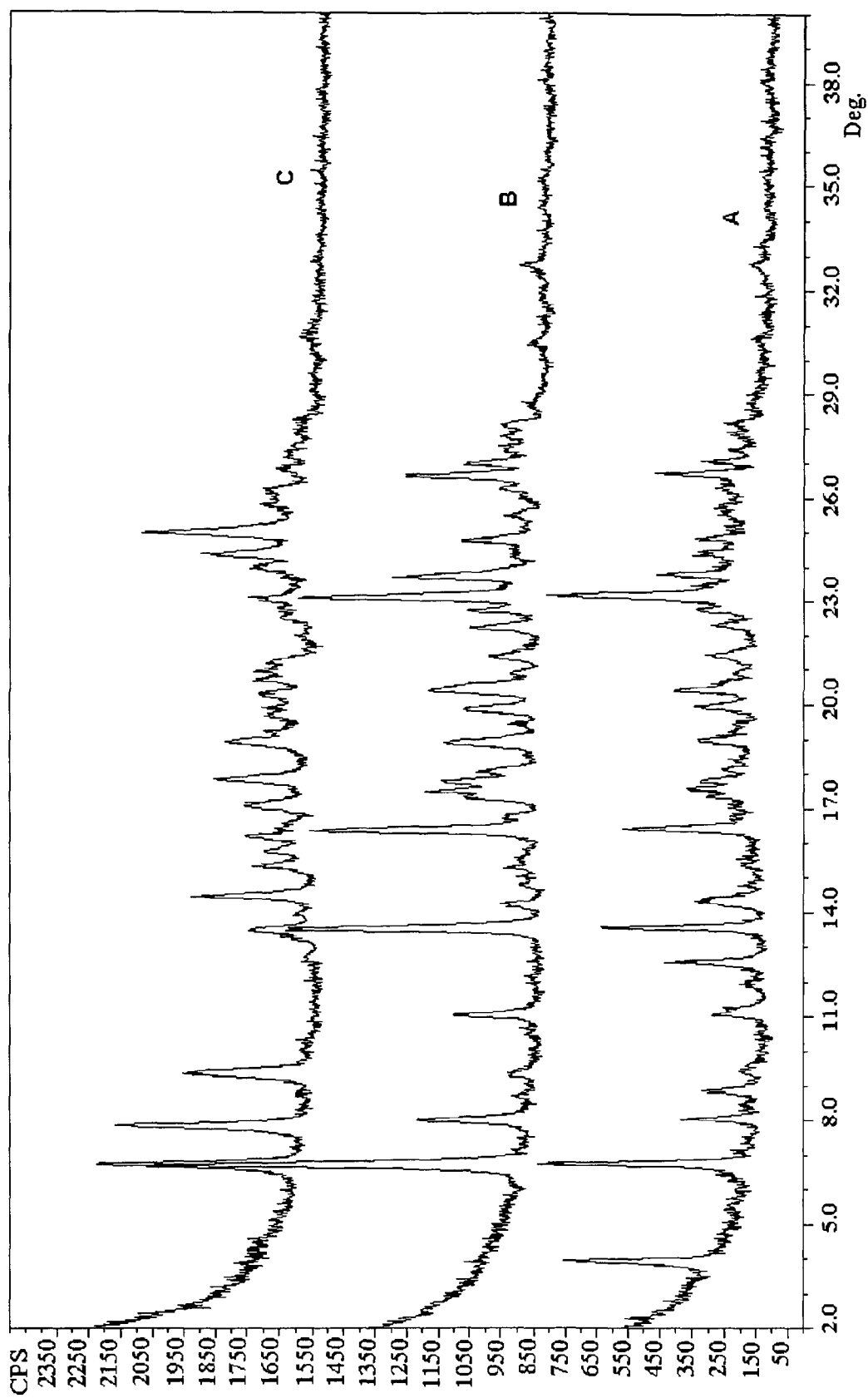
FIG. 6 shows the X-ray diffractogram of compound 937 maleate salt form I (A-B) and maleate salt form II (C).

As a further aspect it has been found that compound 937 maleate salt can be obtained as a crystalline solid in two different crystalline forms named form I and form II. Form I is a high melting crystalline form of compound 937 maleate salt that is characterized as a stable hydrated form. (PXRD profile: FIG. 1F; DSC profile: FIG. 9F; other references about PXRD and DSC profiles are described in table 1). Form II is a high melting crystalline form of compound 937 maleate salt that is characterized as a moderately hygroscopic form (PXRD profile: FIG. 6C; DSC profile: FIG. 10G; DVS profiles: FIG. 13C). Form II undergoes conversion to form I by effect of exposition to stressed conditions of temperature and humidity such as storage at 40° C./75% RH. (PXRD profile: FIG. 6B; DSC profile: FIG. 10F)

Figure 7:
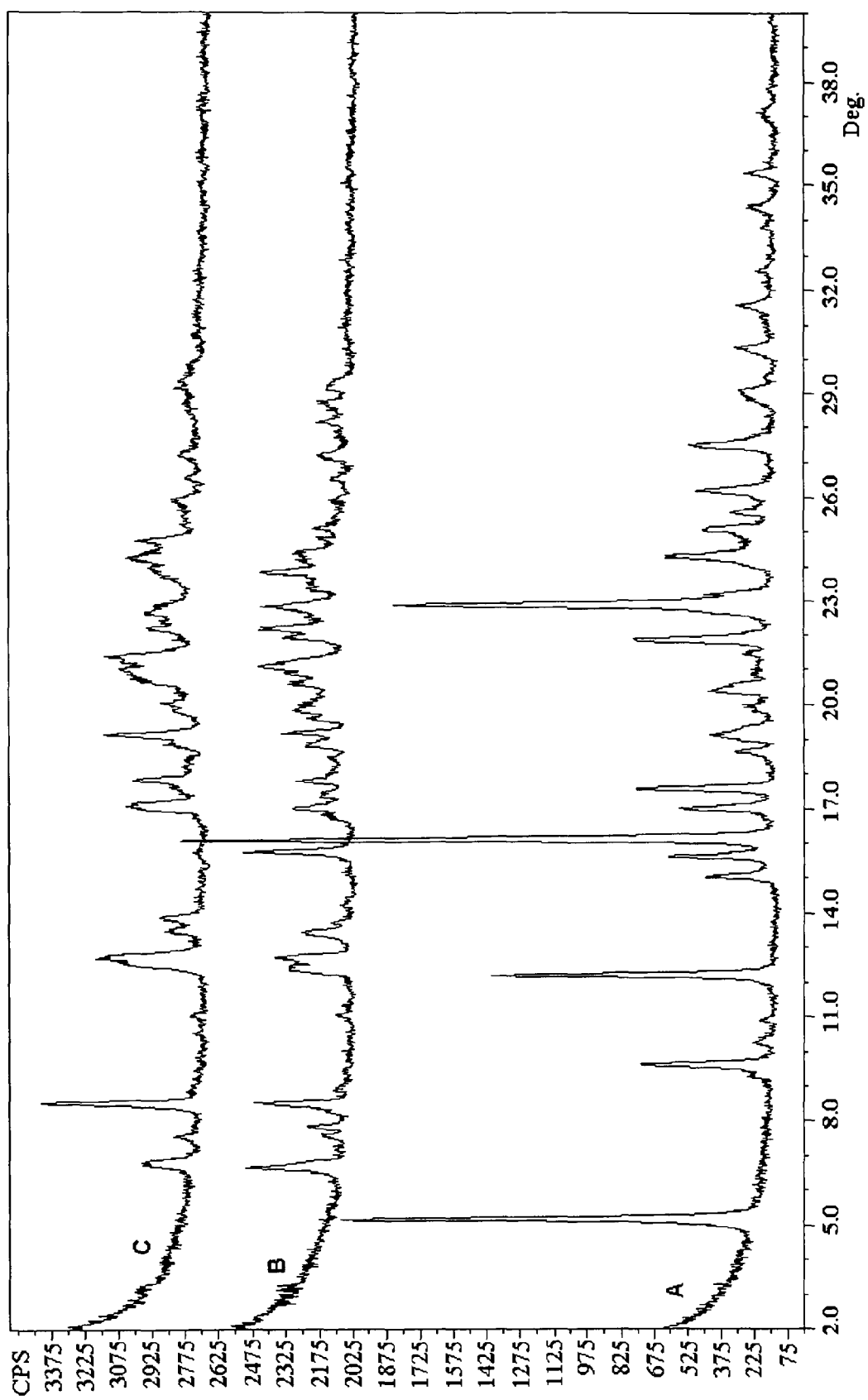
FIG. 7 shows the X-ray diffractogram of compound 937 succinate salt form I (A) and succinate salt form II (B-C).

As a further aspect it has been found that compound 937 succinate salt can be obtained as a crystalline solid in two different crystalline forms named form I and form II. Form I is a high melting crystalline form of compound 937 succinate salt that is characterized as a methanol solvate (PXRD profile: FIGS. 10 and 7A; DSC profile: FIG. 9C). Form II is a high melting crystalline form of compound 937 succinate salt that is characterized as a hydrated form stable at room conditions and stressed conditions of temperature and humidity such as storage at 40° C./75% RH (PXRD profile: FIGS. 7B and 7C; DSC profile: FIGS. 10C and 10D; DVS profiles: FIG. 13D).

Furthermore, it has been found that compound 937 citrate salt can be obtained as a crystalline solid in stoichiometric ratio of 0.5:1 (PXRD profile: FIG. 1K; DSC profile: FIG. 9K) and as an amorphous solid in stoichiometric ratio of 1:1. Compound 937 salts show good aqueous solubility, in particular the solubility of the fumarate, L-malate and L-tartarate salts in water is in the range 1÷4 mg/ml (more details reported in Example 4).

Besides the advantage of exhibiting adequate water solubility, the compound 937 salts, in particular fumarate, L-malate and L-tartarate salts, are also particularly suitable to be manufactured reproducibly in a clear acid/base ratio. This finding renders these salts particularly suitable for the use in liquid formulations for oral as well as for intravenous formulations.

Moreover, Compound 937 salts show favourable powder bulk density, in particular the powder bulk density of the fumarate, L-malate and L-tartarate salts is greater than 240 mg/ml (more details reported in Example 12).

As already mentioned, the description of the solid state properties of the salts and the free base forms of compound 937 together with the complete list of related PXRD and DSC figures are shown in Table 1.

TABLE 1

Description of the solid state properties and Figures/Table references of the salts and free base forms of compound 937

| Compound 937 (*) | Crystalline Form | PXRD Fig. | PXRD Table | Significant PXRD peaks (2-theta, deg) (**) | DSC Fig. |
|---|---|---|---|---|---|
| Fumarate | I | 1J-2C-3-14 | 2 | 14.3, 14.8, 15.3. 15.9, 18.1, 18.5, 20.1, 21.1, 21.5, 22.1, 22.9, 24.0, 24.5, 24.8, 26.8. | 9J-10E-15 |
| Fumarate | II | 16 | 10 | 4.1, 5.3, 5.8, 12.5, 14.4, 15.4, 18.1, 20.1, 22.2, 22.4, 23.0, 24.1, 24.7, 26.0, 26.8 | — |
| L-Tartrate | I | 1B-2B-5 | 3 | 8.3, 12.5, 13.5, 14.4, 16.7, 18.0, 18.3, 18.7, 20.3, 20.6, 21.0, 22.4, 24.1, 28.5, 29.0. | 9B-10B |
| L-Malate | I | 1G-2D-4 | 4 | 6.7, 8.3, 12.4, 13.4, 16.7, 17.4, 18.2, 18.7, 20.1, 20.4, 22.3, 23.5, 23.9, 25.2, 28.3. | 9G-10H |
| Maleate | I | 1F-6A-6B | 5 | 3.9, 6.8, 8.1, 8.9, 12.6, 13.6, 14.3, 16.4, 17.6, 19.0, 20.0, 20.4, 23.2, 23.8, 26.7. | 9F-10F |
| Maleate | II | 6C | 6 | 6.8, 7.9, 9.4, 13.5, 14.5, 15.4, 16.2, 17.1, 17.9, 19.0, 20.0, 20.7, 21.0, 24.4, 25.0. | 10G |
| Succinate | I | 1C-7A | 7 | 5.2, 9.6, 12.2, 15.1, 15.6, 16.1, 17.0, 17.6, 20.4, 21.9, 22.9, 24.3, 25.1, 26.2, 27.5. | 9C |

TABLE 1-continued

Description of the solid state properties and Figures/Table references of the salts and free base forms of compound 937

| Compound 937 (*) | Crystalline Form | PXRD Fig. | PXRD Table | Significant PXRD peaks (2-theta, deg) (**) | DSC Fig. |
|---|---|---|---|---|---|
| Succinate | II | 7B-7C | 8 | 6.8, 8.6, 12.6, 12.8, 13.9, 17.1, 17.9, 19.2, 20.8, 21.1, 21.4, 22.3, 22.8, 24.3, 24.8. | 10C-10D |
| Free base | I | 1A-2A-8-12A-12B | 9 | 3.3, 6.6, 9.1, 9.5, 9.9, 11.1, 12.2, 16.0, 17.4, 18.0, 21.4, 23.5, 24.5, 26.7, 28.2. | 9A-10A1-11A-11B1 |
| Free base | II | — | — | — | 10A2-11B2 |

Note (*): if not differently specified, the described salts are intended in the 1:1 molar ratio between free base and counterion.
Note (**): the reported PXRD peaks have been selected according their higher intensity among the complete dataset.

Figure 3:
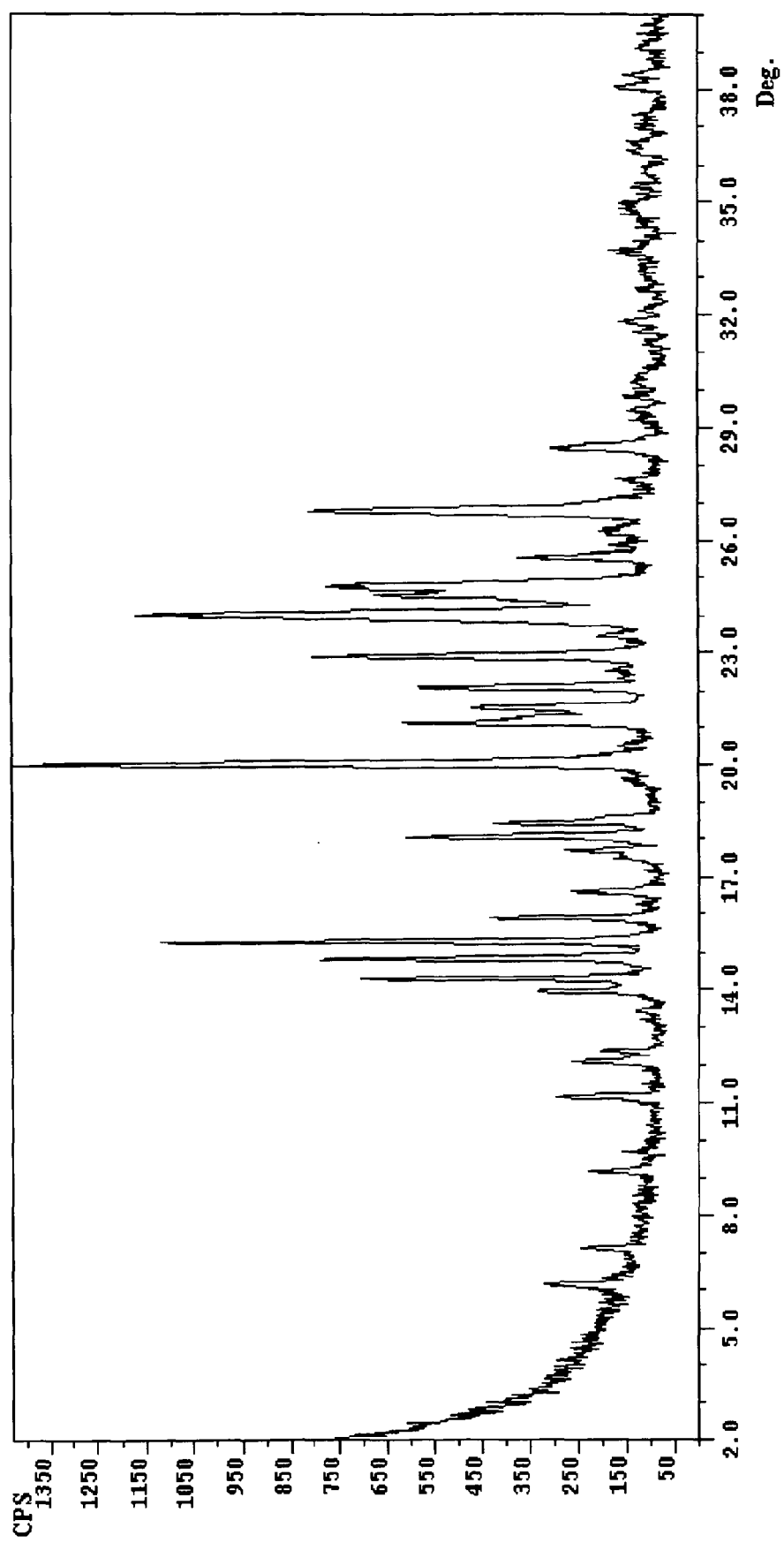
FIG. 3 shows the X-ray diffractogram of compound 937 fumarate salt form I.

In a preferred embodiment, the form I of the essentially pure 1:1 fumarate salt of compound 937 shows the X-ray diffraction diagram indicated in FIG. 3, with significant peak intensities at about the 2-theta values (deg) described in table 1. In samples being free of any additional materials (other crystalline forms, excipients), it should be possible to observe diffraction peaks at about the 2-theta values (deg) described in table 2.

In another preferred embodiment, the form II of the essentially pure 1:1 fumarate salt of compound 937 shows the X-ray diffraction diagram indicated in FIG. 16, with significant peak intensities at about the 2-theta values (deg) described in table 1. In samples being free of any additional materials (other crystalline forms, excipients), it should be possible to observe diffraction peaks at about the 2-theta values (deg) described in table 10.

Figure 4:
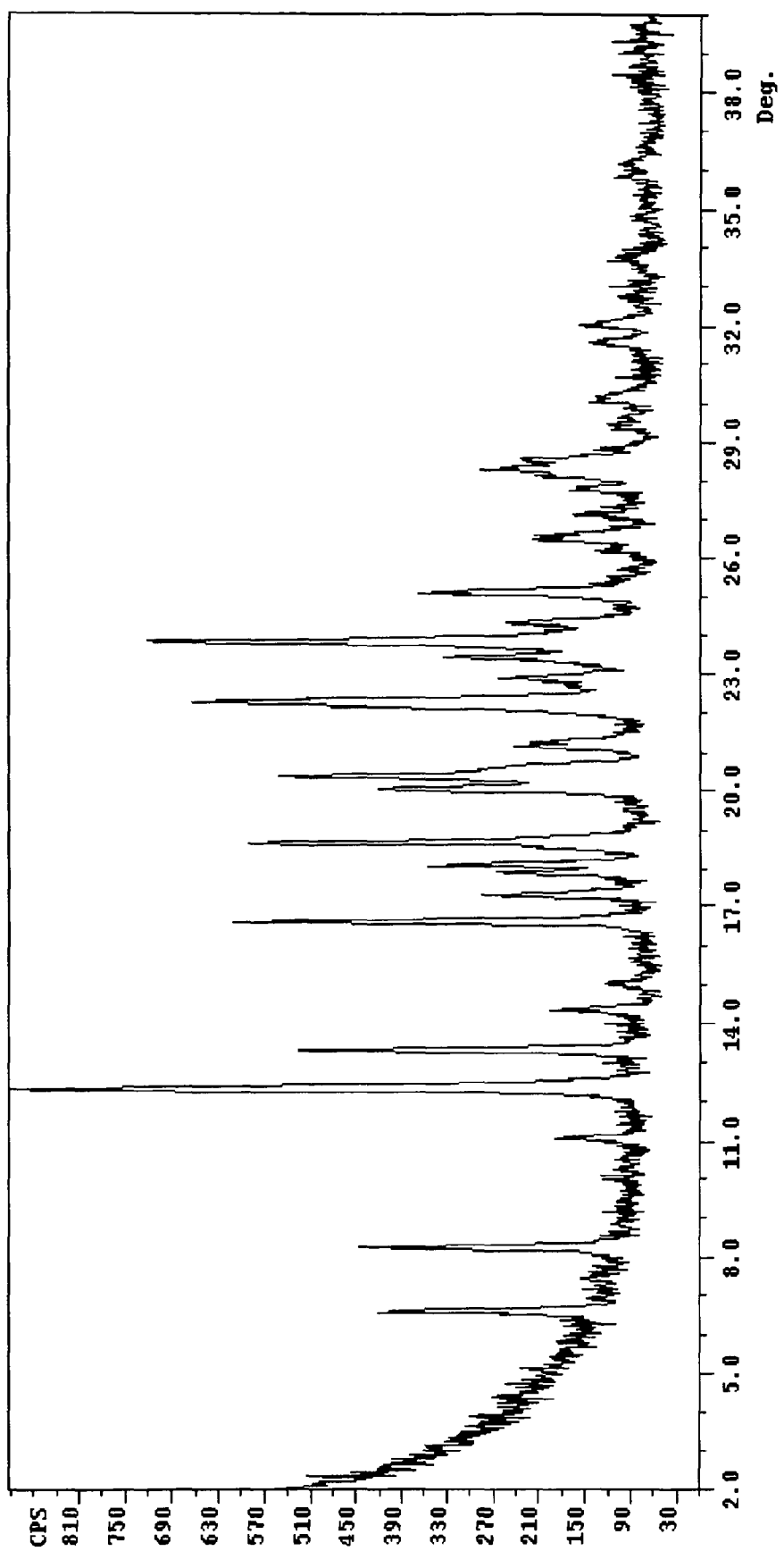
FIG. 4 shows the X-ray diffractogram of compound 937 L-malate salt form I.

In another preferred embodiment, the form I of the essentially pure 1:1 L-malate salt of compound 937 shows the X-ray diffraction diagram indicated in FIG. 4, with significant peak intensities at the 2-theta values (deg) described in table 1. In samples being free of any additional materials (other crystalline forms, excipients), it should be possible to observe diffraction peaks at about the 2-theta values (deg) described in table 4.

Figure 5:
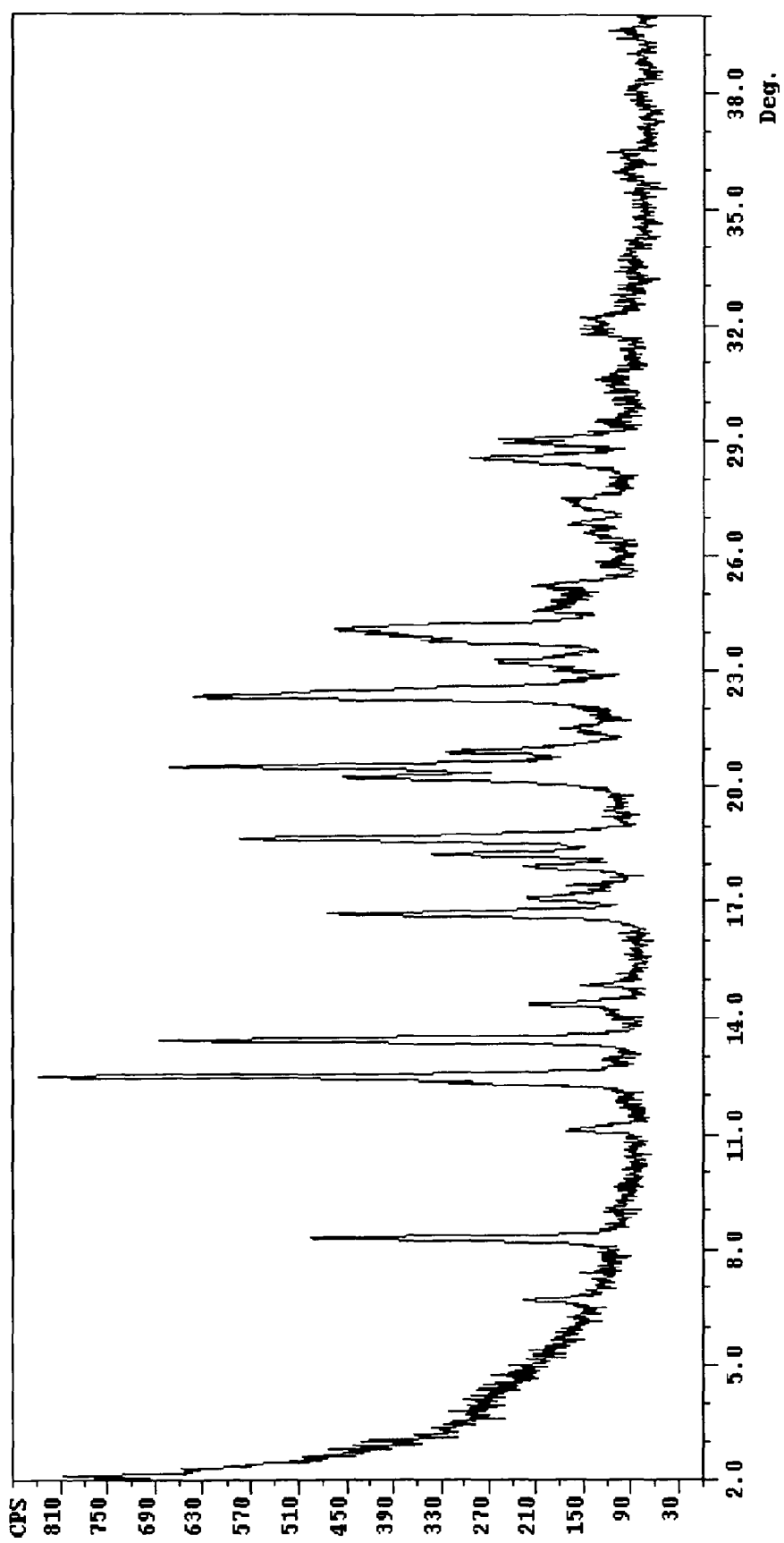
FIG. 5 shows the X-ray diffractogram of compound 937 L-tartrate salt form I.

In another preferred embodiment, the form I of the essentially pure 1:1 L-tartarate salt of compound 937 shows the X-ray diffraction diagram indicated in FIG. 5, with significant peak intensities at the 2-theta values (deg) described in table 1. In samples being free of any additional materials (other crystalline forms, excipients), it should be possible to observe diffraction peaks at about the 2-theta values (deg) described in table 3.

In another preferred embodiment, the form I of the essentially pure 1:1 maleate salt of compound 937 shows the X-ray diffraction diagram indicated in FIG. 6A, with significant peak intensities at the 2-theta values (deg) described in table 1. In samples being free of any additional materials (other crystalline forms, excipients), it should be possible to observe diffraction peaks at about the 2-theta values (deg) described in table 5.

In another preferred embodiment, the form II of the essentially pure 1:1 maleate salt of compound 937 shows the X-ray diffraction diagram indicated in FIG. 6C, with significant peak intensities at the 2-theta values (deg) described in table 1. In samples being free of any additional materials (other crystalline forms, excipients), it should be possible to observe diffraction peaks at about the 2-theta values (deg) described in table 6.

In another preferred embodiment, the form I (methanol solvate) of the essentially pure 1:1 maleate salt of compound 937 shows the X-ray diffraction diagram indicated in FIG. 7A, with significant peak intensities at the 2-theta values (deg) described in table 1. In samples being free of any additional materials (other crystalline forms, excipients), it should be possible to observe diffraction peaks at about the 2-theta values (deg) described in table 7.

In another preferred embodiment, the form II of the essentially pure 1:1 maleate salt of compound 937 shows the X-ray diffraction diagram indicated in FIG. 7C, with significant peak intensities at the 2-theta values (deg) described in table 1. In samples being free of any additional materials (other crystalline forms, excipients), it should be possible to observe diffraction peaks at about the 2-theta values (deg) described in table 8.

Figure 8:
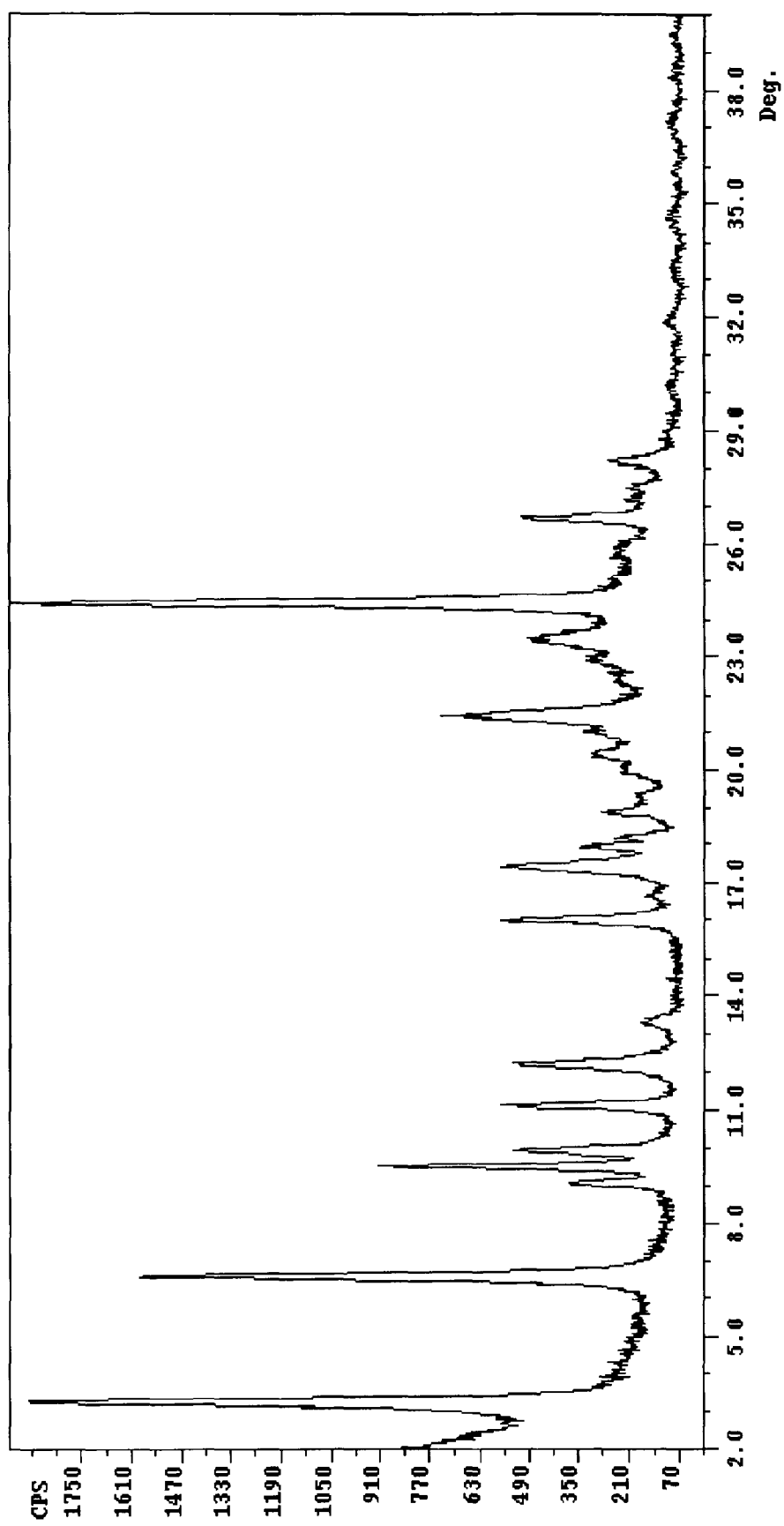
FIG. 8 shows the X-ray diffractogram of compound 937 free base, form I.

In another preferred embodiment, the form I of the essentially pure compound 937 free base shows the X-ray diffraction diagram indicated in FIG. 8, with significant peak intensities at the 2-theta values (deg) described in table 1. In samples being free of any additional materials (other crystalline forms, excipients), it should be possible to observe diffraction peaks at about the 2-theta values (deg) described in table 9.

Figure 9:
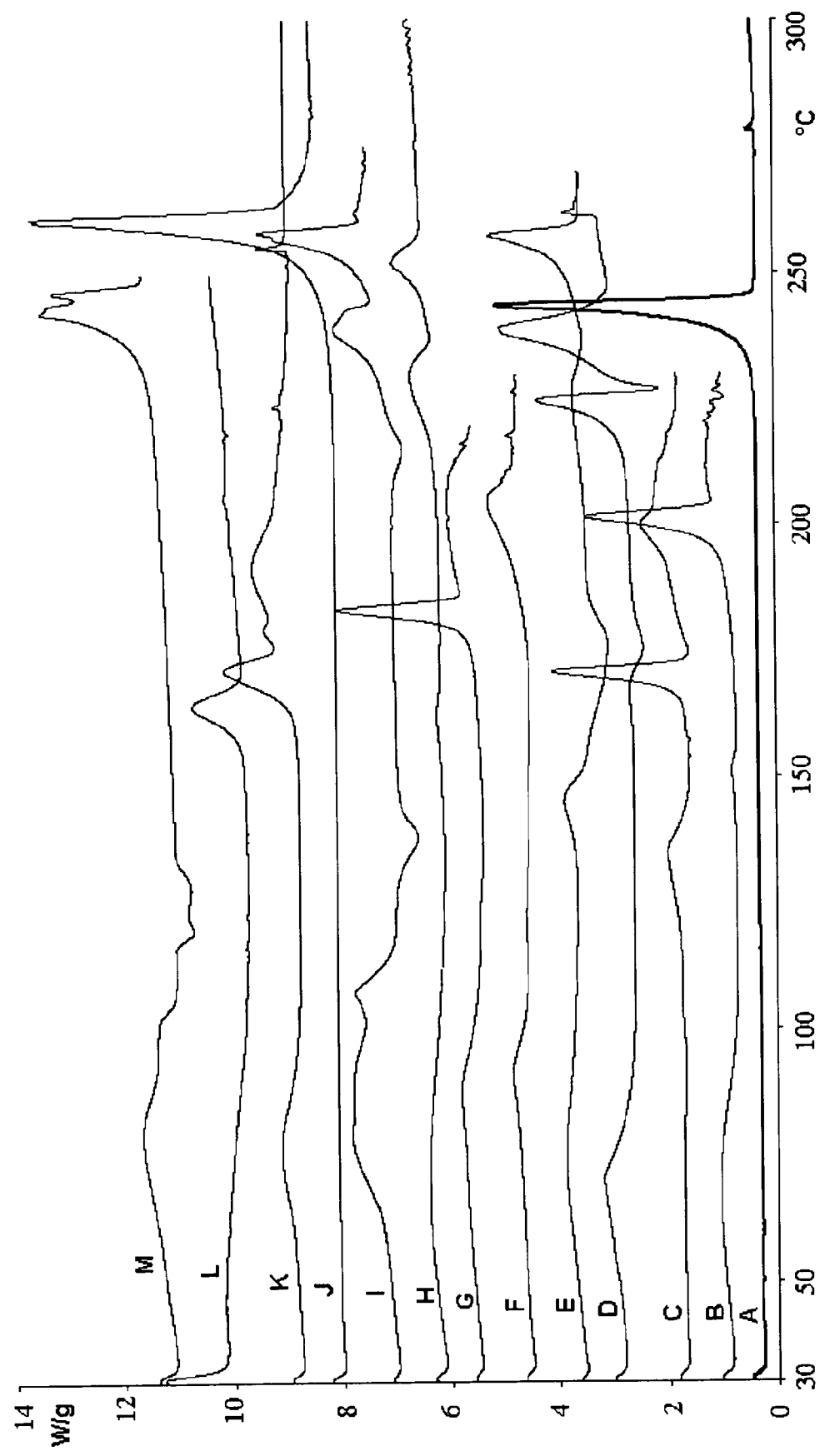
FIG. 9 shows the DSC thermograms of compound 937 free base form I (A) and the following salts: L-tartrate form I (B), succinate form I (C), phosphate form I (D), mesylate form I (E), maleate form I (F), L-malate form I (G), hydrochloride form I (H), fumarate—half mole of counterion form I (I), fumarate form I (J), citrate form I (K), benzenesulfonate form I (L), L-aspartate—half mole of counterion form I (M).

The crystalline structure of form I can thus be characterized by DSC profiles 9A and 10A1 melting endotherms reported in FIG. 9 and FIG. 10, as well as DSC profiles 11A and 11B1 reported in FIG. 11. Another preferred embodiment is the form II of the compound 937 free base which shows the DSC profiles 10A2 and 11B2 respectively reported in FIG. 10 and FIG. 11. The higher melting DSC peak corresponds to form II since freebase batches characterized by thermograms reported in FIGS. 9A and 10A share the same X-ray powder diffraction diagram as reported in FIG. 12.

Essentially pure means that the crystalline forms of the present invention have a purity of at least 90%. More preferably the crystalline forms of the present invention have a purity of at least 95%, and most preferably at least 99% by weight of the acid addition salt or free base of compound 937 are present in the crystalline form according to the invention.

As a further aspect concerning solid state characterization by means of DSC, it has been found that compound 937 fumarate (half mole of counterion), hydrochloride, mesylate and phosphate salts, characterized as crystalline materials by means of PXRD, show complex DSC profile (FIG. 9). Such salts undergo thermal transitions involving desolvation/dehydration processes and subsequent melting of desolved/dehydrated forms characterized by their DSC melting peak temperatures.

Further thermal transitions may follow when e.g. degradation occurs.

PXRD and DSC results are further described in table 1 and examples 6 and 7.

According to a further aspect of the invention a pharmaceutical composition can be formulated according to known method in the art in any of the pharmaceutical forms known in the art for administration to a mammal, including humans.

For instance, a pharmaceutical composition which comprises a salt of compound 937, as defined herein in association with a pharmaceutically acceptable diluent or carrier.

The compositions of the invention may be in a form suitable for oral use. Examples of these forms are: tablets, hard or soft capsules, aqueous or oily suspensions, emulsions, dispersible powders or granules. The compositions of the invention may also be in a form suitable for topical use. Examples of these forms are: creams, ointments, gels, or aqueous or oily solutions or suspensions. The compositions of the invention may also be in a form suitable for administration by inhalation such as, for example, finely divided powder or a liquid aerosol. The compositions of the invention may also be in a form suitable for administration by insufflation such as, for example, finely divided powder. The compositions of the invention may also be in a form suitable for parenteral administration (such as, for example, a sterile aqueous or oily solution for intravenous, subcutaneous, intramuscular) or as a suppository for rectal dosing. The compositions of the invention may be obtained by conventional procedures using conventional pharmaceutical excipients, well known in the art.

Thus, compositions intended for oral use may contain one or more additives such as, for example, colouring, sweetening, flavouring and preservative agents.

Suitable pharmaceutically acceptable excipients in the formulation of a tablet include can be, for example, fillers such as lactose, mannitol, microcrystalline cellulose, sodium carbonate, pregelatinized starch, calcium phosphate or calcium carbonate; granulating and disintegrating agents such as sodium croscarmellose, corn starch, crospovidone or sodium starch glycolate; binding agents such as starch, microcrystalline cellulose, povidone, sucrose; lubricating agents such as magnesium stearate, stearic acid, sodium stearyl fumarate, glyceryl behenate, polyethylene glycols or talc; glidants, such as colloidal silicon dioxide; preservative agents such as ethyl or propyl p-hydroxybenzoate, and anti-oxidants such as ascorbic acid.

Tablet formulations may be uncoated or submitted to a coating process, to modify their disintegration properties and the subsequent absorption of the active ingredient in the gastrointestinal track, to improve stability or appearance. Uncoated and coated tablets require the use of conventional coating agents and/or procedures well known in the art. Compositions for oral use may be formulated as hard gelatin capsules where the filling mixture is prepared with the active ingredient that is mixed with an inert solid diluent, for example, calcium carbonate, calcium phosphate or kaolin and including the above mentioned excipients for tablet formulations. Compositions for oral use may also be formulated as soft gelatin capsules where the filling mixture is prepared with the active ingredient that is mixed with water or an oil such as peanut oil, liquid paraffin, soya bean oil, coconut oil, or preferably olive oil, or other acceptable vehicle. Compositions for oral use may also be in the form of hard gelatin capsules in which the active ingredient is formulated as a stable pharmaceutical solid or semisolid dispersion comprising the active ingredient and, for example, a hydrophilic carrier, a water-soluble vitamin E derivative as antioxidant agent and optionally other excipients. Aqueous suspensions are generally prepared with the finely powdered active ingredient in together with the addition of one suspending agents, (such as, for example sodium carboxymethylcellulose, methylcellulose, hydroxypropylmethylcellulose, sodium alginate, polyvinyl-pyrrolidone) dispersing or wetting agents (such as, for example, lecithin, polyoxyethylene stearate, or polyoxyethylene sorbitol monooleate, polyethylene sorbitan monooleate). The aqueous suspensions may also contain one or more suitable additives such as preservatives, anti-oxidants, colouring agents, flavouring and/or sweetening agents to provide a palatable oral preparation. Oily suspensions may be obtained by suspending the active ingredient in a suitable vegetable oil (such as, for example, olive oil and sesame oil). Dispersible or lyophilised powders as well as granules suitable for preparation of an aqueous suspension or solution by the addition of water contain the active ingredient and suitable excipients (bulking, dispersing or suspending agents and preservatives).

The formulation may also be a sterile injectable suspension, solution, emulsion prepared according to known procedures using appropriate excipients selected, for example, among the above mentioned dispersing, wetting and suspending agents.

Topical formulations, such as creams, ointments, gels, solutions or suspensions, may be prepared by formulating an active ingredient with a conventional, vehicle or diluent using conventional procedure well known in the art.

Compositions for administration by insufflation may be finely divided powder containing particles of suitable average diameter of, for example, 50 µm or less, the powder itself composed by either active ingredient as is or diluted with suitable carriers such as lactose.

The powder for insufflation is formulated in a capsule containing a suitable amount of active to be used with a turbo-inhaler device. Compositions for administration by inhalation may be in the form of a conventional pressurised aerosol arranged to dispense the active ingredient either as an aerosol containing finely divided solid or liquid droplets.

Conventional aerosol propellants and devices may be used to dispense a defined quantity of active ingredient. Examples of compositions for oral use in the form of hard gelatin capsules are described in example 10.

EXAMPLES

The following Examples illustrate the invention.
Temperatures are measured in degrees Celsius (° C.).
Unless otherwise indicated, the reactions or experiments take place at room temperature.

ABBREVIATIONS

RT: room temperature
RH: relative humidity
PXRD: Powder X-Ray diffraction
DSC: Differential Scanning calorimetry
DVS: Dynamic Vapor Sorption
TGA: Thermogravimetric Analysis

Example 1

Low Scale Preparation of Compound 937 Salts

An aliquot of compound 937 free base (about 40÷50 mg) was dissolved at RT in 4÷5 mL of a 2:1 mixture of methanol and dichloromethane, obtaining a nominal concentration of about 10 mg/mL.

Several experiments of salt formation were then performed by addition of 1:1 stoichiometric amounts of the counterions to 4÷5 mL of the described compound 937 free base solution at RT.

Cooling crystallization experiments at −30° C. were performed with resting times of about 24-36 h.

The obtained precipitates were collected by vacuum filtration and dried at 40° C. under vacuum.

When crystallization did not occur, the solutions were concentrated by evaporating at RT under a mild nitrogen flow to allow precipitation.

In some cases, a further step of re-crystallization (e.g. compound triturated in diethylether) was required to isolate a crystalline or at least powdery sample starting from a gluey residue.

Drying was allowed at 40° C. under vacuum conditions.

Chemical identification of compound 937 and acidic counterion was performed by $^1$H NMR (described in example 9).

Example 2

Gram-Scale Preparation of Compound 937 L-Tartrate, Succinate, Fumarate, Citrate, Maleate and L-Malate Salts The free base (500 mg, 0.939 mmol) was dissolved in a 2:1 mixture of dichloromethane:methanol (24 mL) at room temperature, then 1 equivalent of the acidic counterion dissolved in methanol or 96% ethanol in case of the fumaric acid was added. The solutions were reduced to 10 mL in vacuo and then cooled down to −20° C. The precipitated materials were then filtered washed with diethyl ether and finally dried for at least 24 hrs at 40° C. under vacuum.

Example 3

Scaled Up Preparation of Compound 937 Fumarate Salt, Form I

An amount of compound 937 free base was heated at reflux and under stirring in absolute ethanol for 30 min allowing complete dissolution of the starting material (concentration of about 25 g/L).

After that time about 1 equivalent of fumaric acid was dissolved in ethanol (concentration of about 29 g/L) and added to the free base solution.

After 30 min at reflux to achieve complete salification, the heating was interrupted.

The mixture was cooled to about 5° C., stirred for about 1 hour at that temperature, filtered washing with absolute ethanol, and then dried under vacuum at 35-40° C.

The obtained material was the ethanol solvate of compound 937 fumarate salt.

Example 4

Scaled Up Preparation of Compound 937 Fumarate Salt, Form II

An amount of compound 937 free base was stirred at RT in water, after 30 min about 1 equivalent of fumaric acid was added.

The suspension is stirred for 2 hours, then cooled to 4° C. and kept at that temperature for 1 hour before filtration.

The obtained material was washed on the filter with cold water and dried under vacuum at 35-40° C.

Example 5

Solubility of Compound 937 Salts and Free Base

The determination of solubility of compound 937 salts, prepared as described in example 2, has been performed by means of the following procedure: known amounts of compound 937 salts and free base stirred for 4 hours at RT in water, in condition of excess solid considering a target concentration of 10 mg/ml. The obtained preparations have been filtered and analyzed by means of HPLC.

The results are here below reported.

The aqueous solubility value of the compound 937 free base according to the above described method is <0.1 mg/mL.

The aqueous solubility value of the compound 937 L-tartrate salt according to the above described method is 1.9 mg/mL.

The aqueous solubility value of the compound 937 succinate salt according to the above described method is 5.8 mg/mL.

The aqueous solubility value of the compound 937 maleate salt according to the above described method is 3.1 mg/mL.

The aqueous solubility value of the compound 937 L-malate salt according to the above described method is 3.9 mg/mL.

The aqueous solubility value of the compound 937 fumarate salt according to the above described method is 0.7 mg/mL.

Example 6

Analytical results by means of Powder X-ray Diffraction (PXRD)

The compound 937 salts were characterized by powder X-Ray Diffraction (PXRD) performed using a Thermo/ARL XTRA apparatus, irradiating powder samples with a CuKα source (45 kV, 40 mA, 1.8 kW-Kα1 radiation, wavelength λ=1.54060 Angstrom) between 5° and 34° 2-theta at room temperature.

The scan rate was of 1.20°/min (0.020° step with count time of 1 seconds per step).

In the X-Ray diffractograms, the angles of diffraction 2-theta are plotted on the horizontal axis (x-axis) and the line intensity on the vertical (y-axis).

In the paragraphs defining the X-ray powder diffraction peaks for the crystalline forms of the salts and free base of compound 937, the term 'at about' is used in the expression '... at about 2-theta angles reported in table...' to indicate that the precise positions of peaks (i.e. the recited 2-theta angle values) should not be considered as being absolute values because, as will be appreciated by those skilled in the art, the precise position of the peaks may vary slightly between one machine and another, from one sample to another, or as a result of slight variations in measurement conditions utilised.

It is also stated in the preceding paragraphs that the crystalline forms of the salts and free base of compound 937 provide X-ray powder diffraction patterns 'substantially' the same as the X-ray powder diffraction patterns shown in FIGS. 1, 2, 3, 4, 5, 6, 7, 8, 12, 14 and 16 have substantially the most prominent peaks at the 2-theta angle values shown in tables 1, 2, 3, 4, 5, 6, 7, 8, 9 and 10. It shall be appreciated that the use of the term 'substantially' in this context is also intended to indicate that the 2-theta angle values of the X-ray powder diffraction patterns may vary slightly from one machine to another, from one sample to another, or as a result of slight variations in measurement conditions, so the peak positions shown in the figures or quoted in the tables are again not to be as absolute values. In this regard, it is known in the art that an X-ray powder diffraction pattern may be obtained which has one or more measurement errors depending on measurement conditions (such as, for example, equipment and/or sample preparation). In particular, it is generally known that intensities in an X-ray powder diffraction pattern may vary depending on measurement conditions and sample preparation.

For example, persons skilled in the art of X-ray powder diffraction will realise that the relative intensity of peaks can be affected by, for example, grains above 30 microns in size and non-unitary aspect ratios, which may affect analysis of samples.

The skilled person will also realise that the position of reflections can be affected by the precise height at which the sample sits in the diffractometer and the zero calibration of the diffractometer.

The surface planarity of the sample may also affect the result.

Hence a person skilled in the art will appreciate that the diffraction pattern data presented herein is not to be considered as absolute (for further information see "Fundamentals of Powder Diffraction and Structural Characterization, Pecharsky and Zavalij, Kluwer Academic Publishers, 2003). Therefore, it shall be understood that the crystalline form of the salts and free base of compound 937 described in the present invention is not limited to the crystals that provide X-ray powder diffraction patterns identical to the X-ray powder diffraction patterns shown e.g. in FIG. 1 and any crystals providing X-ray powder diffraction patterns substantially the same as that shown e.g. in FIG. 1 fall within the scope of the present invention.

A person skilled in the art of X-ray powder diffraction is able to judge the substantial identity of X-ray powder diffraction patterns.

Generally, a measurement error of a diffraction angle in an X-ray powder diffractogram is about 2-theta=0.5 deg or less (or, more suitably, about 2-theta=0.2 deg or less) and such degree of a measurement error should be taken into account when considering the X-ray powder diffraction pattern in FIGS. 1, 2, 3, 4, 5, 6, 7, 8, 12, 14 and 16, and when interpreting the peak positions referred to both in the text and in tables 1, 2, 3, 4, 5, 6, 7, 8, 9 and 10.

Therefore, where it is stated, for example, that the salts and free base of compound 937 have an X-ray powder diffraction pattern with at least one specific peak at about 2-theta=20.1 deg (or any one of the other mentioned angles) then this can be interpreted as being 2-theta=20.1 deg plus or minus 0.5 deg, or 2-theta=20.1 deg plus or minus 0.2 deg.

Figure 1:
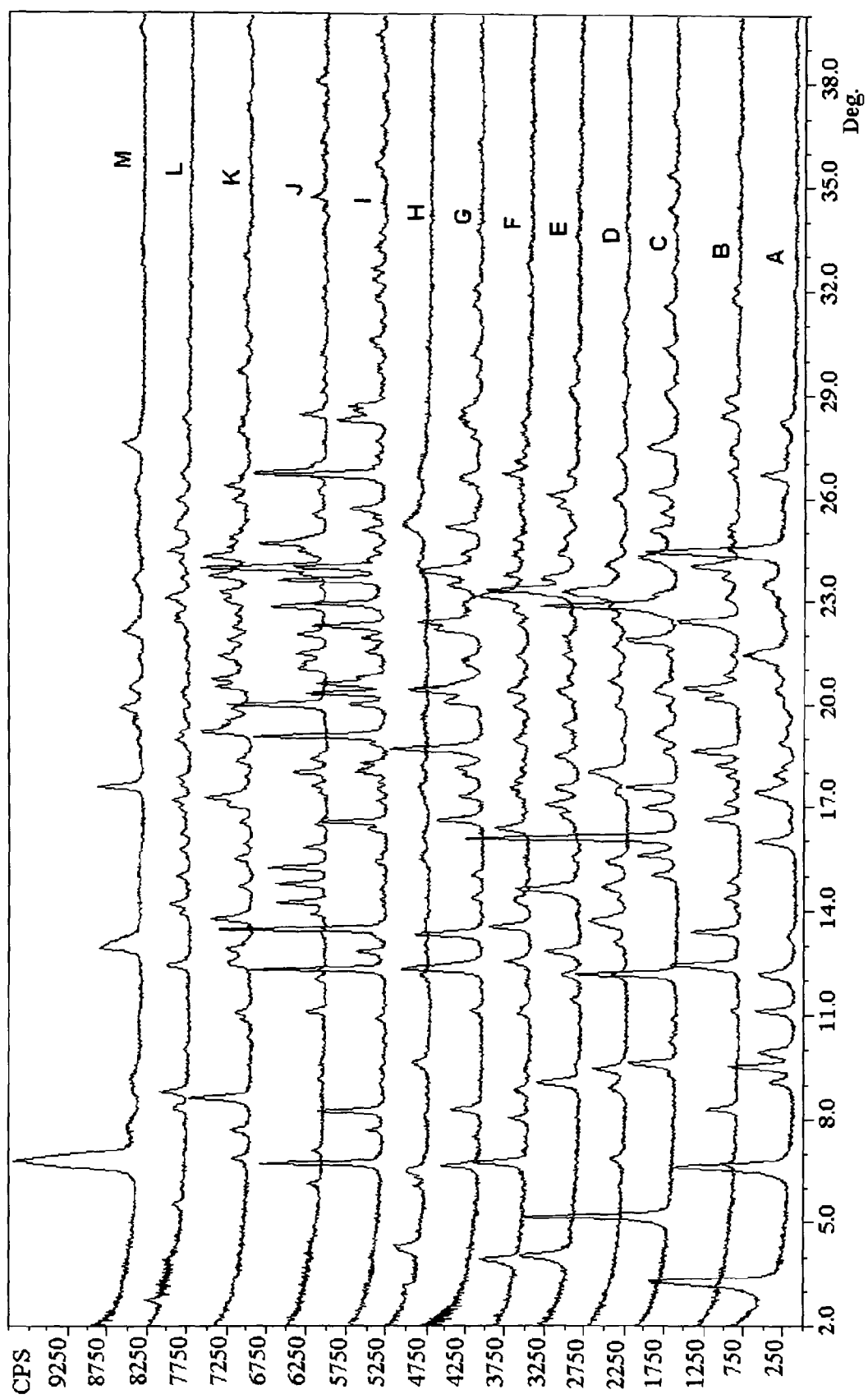
FIG. 1 shows the X-ray diffractograms of compound 937 free base and its crystalline salts reporting 2-theta angles (deg) on the x axis while intensity (CPS) is reported on the y axis. In particular the spectra refers to compound 937 free base form I (A) and the following salts: L-tartrate form I (B), succinate form I (C), phosphate form I (D), mesylate form I (E), maleate form I (F), L-malate form I (G), hydrochloride form I (H), fumarate—half mole of counterion form I (I), fumarate form I (J), citrate—half mole of counterion form I (K), benzenesulfonate form I (L), L-aspartate—half mole of counterion form I (M).

FIG. 1 reports powder X-Ray diffractograms of the salts of compound 937 isolated at low scale as described in example 1, and of the free base.

Figure 2:
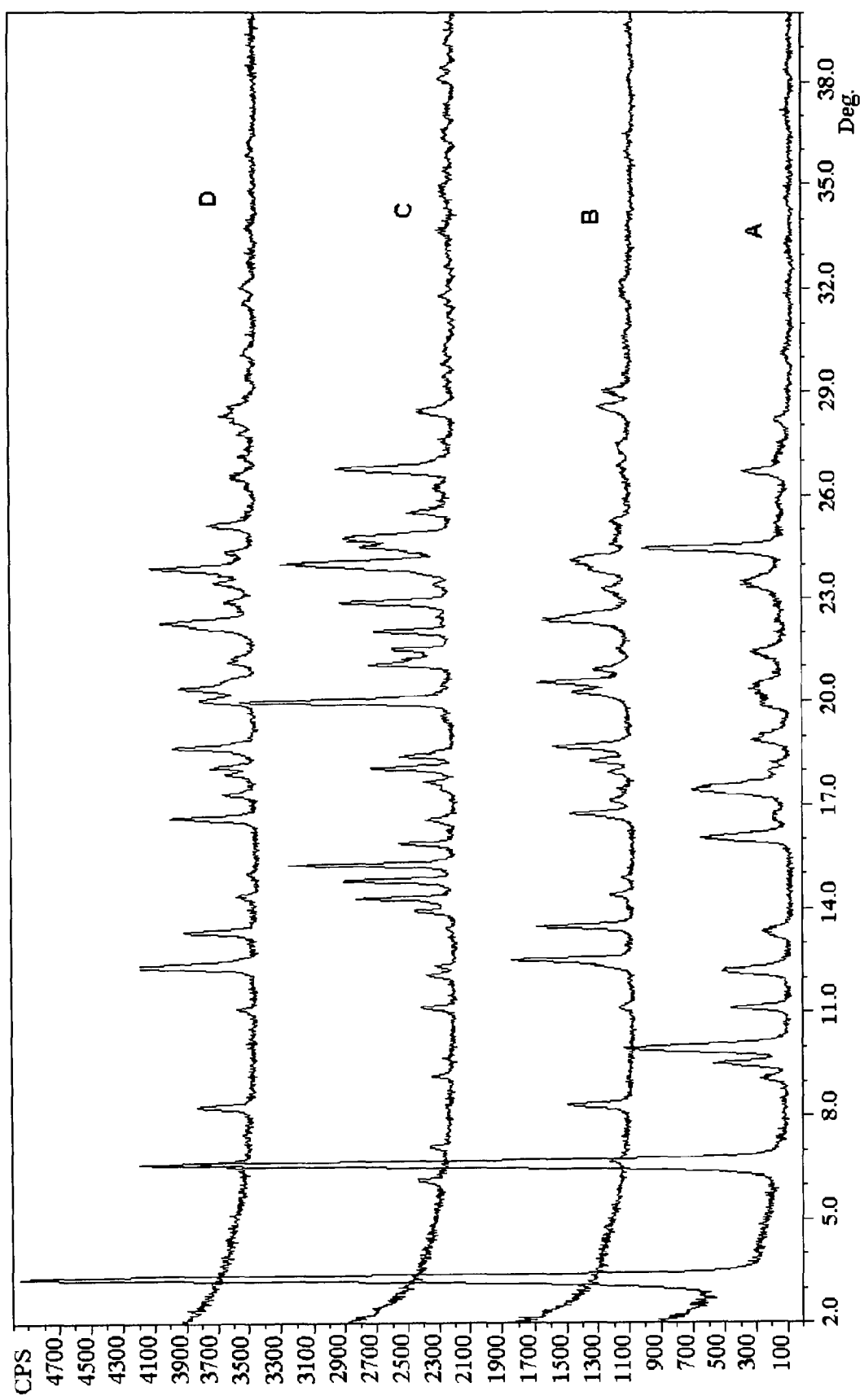
FIG. 2 shows the X-ray diffractograms of compound 937 free base form I (A) and the following salts: L-tartrate form I (B), fumarate form I (C), L-malate form I (D) salts.

FIG. 2 reports examples of powder X-ray diffractograms of the salts of compound 937 obtained at a larger scale as described in example 2: L-tartrate form I (B), fumarate form I (C) and L-malate form I (D) salts.

The X-ray diffraction peaks of compound 937 fumarate salt form I, L-malate salt form I, L-tartrate salt form I, maleate salt form I (A-B), maleate salt form II (C), succinate salt form I (A) and succinate salt form II (B-C) are reported in FIGS. 3, 4, 5, 6 and 7 respectively.

FIG. 8 reports the X-ray diffraction peaks of compound 937 free base form I.

FIG. 12 reports the X-ray diffraction peaks of compound 937 free base form I (A-B) related to the same batches characterized by the DSC profiles reported in FIG. 9, FIG. 10 and FIG. 11 (DSC data are also discussed in example 6). The main X-ray diffraction peaks 2-theta angles of compound 937 fumarate salt form I, L-tartate salt form I, L-malate salt form I, maleate salt form I and maleate salt form II, succinate salt form I, succinate salt form II, free base and fumarate salt form II are reported in Table 2, 3, 4, 5, 6, 7, 8, 9 and 10 respectively.

The PXRD profile of a scaled-up batch of the compound 937 fumarate salt form I, obtained according to example 3, is reported in FIG. 14.

The PXRD profile of a scaled-up batch of the compound 937 fumarate salt form II, obtained according to example 4, is reported in FIG. 16.

TABLE 2

Compound 937 fumarate salt, form I

| Position (Deg.) | Intensity (CPS) | Relative Intensity (%) |
|---|---|---|
| 6.2 | 117.5 | 12.2 |
| 7.1 | 73.1 | 7.6 |
| 9.2 | 84.8 | 8.8 |
| 11.2 | 135.8 | 14.1 |
| 12.1 | 102.5 | 10.7 |
| 12.4 | 64.5 | 6.7 |
| 14.0 | 163.5 | 17.0 |
| 14.3 | 404.4 | 42.1 |
| 14.8 | 488.9 | 50.9 |
| 15.3 | 742.8 | 77.3 |
| 15.9 | 242.8 | 25.3 |
| 16.6 | 106.7 | 11.1 |
| 17.7 | 98.8 | 10.3 |
| 18.1 | 355.6 | 37.0 |
| 18.5 | 269.7 | 28.1 |
| 20.1 | 961.1 | 100.0 |
| 21.1 | 351.4 | 36.6 |
| 21.5 | 219.3 | 22.8 |
| 22.1 | 341.0 | 35.5 |
| 22.9 | 498.4 | 51.9 |
| 24.0 | 646.5 | 67.3 |
| 24.5 | 316.5 | 32.9 |
| 24.8 | 429.0 | 44.6 |
| 25.5 | 167.6 | 17.4 |
| 26.2 | 71.4 | 7.4 |
| 26.8 | 479.6 | 49.9 |
| 28.5 | 145.3 | 15.1 |
| 33.7 | 40.5 | 4.2 |
| 38.1 | 72.7 | 7.6 |
| 38.4 | 65.7 | 6.8 |

TABLE 3

Compound 937 L-tartrate salt, form I

| Position (Deg.) | Intensity (CPS) | Relative Intensity (%) |
|---|---|---|
| 6.7 | 56.0 | 11.7 |
| 8.3 | 267.3 | 55.7 |
| 11.1 | 50.3 | 10.5 |
| 12.5 | 479.9 | 100.0 |
| 13.5 | 399.5 | 83.3 |
| 14.4 | 88.8 | 18.5 |
| 14.9 | 35.0 | 7.3 |
| 16.7 | 239.1 | 49.8 |
| 17.1 | 74.3 | 15.5 |
| 17.5 | 57.3 | 11.9 |
| 18.0 | 76.2 | 15.9 |
| 18.3 | 163.1 | 34.0 |
| 18.7 | 317.8 | 66.2 |
| 20.3 | 213.9 | 44.6 |
| 20.6 | 348.5 | 72.6 |
| 21.0 | 135.9 | 28.3 |
| 21.6 | 49.5 | 10.3 |
| 22.4 | 329.8 | 68.7 |

TABLE 3-continued

Compound 937 L-tartrate salt, form I

| Position (Deg.) | Intensity (CPS) | Relative Intensity (%) |
|---|---|---|
| 23.3 | 73.8 | 15.4 |
| 24.1 | 196.8 | 41.0 |
| 24.6 | 59.9 | 12.5 |
| 24.8 | 33.4 | 7.0 |
| 25.2 | 54.3 | 11.3 |
| 26.9 | 45.0 | 9.4 |
| 27.4 | 36.2 | 7.5 |
| 28.5 | 117.1 | 24.4 |
| 29.0 | 83.5 | 17.4 |
| 31.8 | 41.3 | 8.6 |
| 32.0 | 34.6 | 7.2 |
| 32.2 | 37.0 | 7.7 |

TABLE 4

Compound 937 L-malate salt, form I

| Position (Deg.) | Intensity (CPS) | Relative Intensity (%) |
|---|---|---|
| 6.7 | 184.0 | 32.9 |
| 8.3 | 224.4 | 40.2 |
| 11.1 | 58.7 | 10.5 |
| 12.4 | 558.9 | 100.0 |
| 13.4 | 310.5 | 55.6 |
| 14.4 | 62.1 | 11.1 |
| 15.1 | 26.5 | 4.8 |
| 16.7 | 369.2 | 66.1 |
| 17.4 | 128.3 | 23.0 |
| 17.9 | 117.1 | 21.0 |
| 18.2 | 172.0 | 30.8 |
| 18.7 | 365.1 | 65.3 |
| 20.1 | 209.0 | 37.4 |
| 20.4 | 287.0 | 51.4 |
| 21.2 | 80.5 | 14.4 |
| 22.3 | 325.2 | 58.2 |
| 22.9 | 80.2 | 14.4 |
| 23.5 | 127.8 | 22.9 |
| 23.9 | 413.5 | 74.0 |
| 24.4 | 89.1 | 15.9 |
| 25.2 | 185.4 | 33.2 |
| 26.6 | 79.3 | 14.2 |
| 27.2 | 44.2 | 7.9 |
| 27.8 | 53.3 | 9.5 |
| 28.2 | 80.4 | 14.4 |
| 28.3 | 141.1 | 25.2 |
| 28.6 | 89.7 | 16.1 |
| 28.9 | 46.2 | 8.3 |
| 30.1 | 52.3 | 9.4 |
| 30.2 | 34.7 | 6.2 |
| 31.6 | 40.6 | 7.3 |
| 32.1 | 56.7 | 10.1 |
| 33.8 | 21.0 | 3.8 |
| 35.9 | 30.3 | 5.4 |
| 36.2 | 14.9 | 2.7 |

TABLE 5

Compound 937 maleate salt, form I

| Position (Deg.) | Intensity (CPS) | Relative Intensity (%) |
|---|---|---|
| 3.9 | 313.9 | 72.7 |
| 4.7 | 24.8 | 5.7 |
| 6.8 | 431.7 | 100.0 |
| 8.1 | 127.2 | 29.5 |
| 8.5 | 18.2 | 4.2 |
| 8.9 | 97.5 | 22.6 |
| 9.5 | 29.6 | 6.9 |

TABLE 5-continued

Compound 937 maleate salt, form I

| Position (Deg.) | Intensity (CPS) | Relative Intensity (%) |
|---|---|---|
| 11.1 | 82.0 | 19.0 |
| 12.0 | 21.4 | 5.0 |
| 12.6 | 160.4 | 37.2 |
| 13.6 | 338.9 | 78.5 |
| 14.3 | 112.1 | 26.0 |
| 16.4 | 245.4 | 56.9 |
| 17.4 | 65.4 | 15.2 |
| 17.6 | 109.8 | 25.4 |
| 17.8 | 83.4 | 19.3 |
| 18.1 | 36.4 | 8.4 |
| 19.0 | 96.7 | 22.4 |
| 20.0 | 95.2 | 22.0 |
| 20.4 | 160.7 | 37.2 |
| 21.4 | 75.5 | 17.5 |
| 22.3 | 60.5 | 14.0 |
| 22.8 | 73.8 | 17.1 |
| 23.2 | 387.2 | 89.7 |
| 23.8 | 149.2 | 34.6 |
| 24.4 | 64.0 | 14.8 |
| 24.8 | 84.1 | 19.5 |
| 25.5 | 37.9 | 8.8 |
| 25.8 | 32.3 | 7.5 |
| 26.3 | 34.7 | 8.0 |
| 26.7 | 178.4 | 41.3 |
| 27.1 | 90.4 | 20.9 |
| 27.4 | 53.9 | 12.5 |
| 27.9 | 32.3 | 7.5 |
| 28.2 | 57.9 | 13.4 |
| 32.7 | 30.0 | 6.9 |

TABLE 6

Compound 937 maleate salt, form II

| Position (Deg.) | Intensity (CPS) | Relative Intensity (%) |
|---|---|---|
| 6.8 | 412.1 | 97.4 |
| 7.9 | 380.9 | 90.0 |
| 9.4 | 249.7 | 59.0 |
| 13.5 | 110.3 | 26.1 |
| 14.5 | 219.0 | 51.7 |
| 15.4 | 83.4 | 19.7 |
| 15.8 | 65.3 | 15.4 |
| 16.2 | 115.8 | 27.4 |
| 16.5 | 40.2 | 9.5 |
| 16.6 | 22.2 | 5.3 |
| 17.1 | 103.9 | 24.6 |
| 17.9 | 172.0 | 40.7 |
| 19.0 | 127.2 | 30.1 |
| 19.3 | 67.3 | 15.9 |
| 19.7 | 46.6 | 11.0 |
| 20.0 | 132.6 | 31.3 |
| 20.3 | 60.6 | 14.3 |
| 20.7 | 199.8 | 47.2 |
| 21.0 | 137.6 | 32.5 |
| 21.3 | 62.4 | 14.8 |
| 22.6 | 25.3 | 6.0 |
| 22.7 | 25.9 | 6.1 |
| 23.1 | 71.0 | 16.8 |
| 24.0 | 68.1 | 16.1 |
| 24.4 | 154.9 | 36.6 |
| 25.0 | 423.2 | 100.0 |
| 25.8 | 50.6 | 12.0 |
| 26.2 | 55.1 | 13.0 |
| 26.9 | 38.0 | 9.0 |
| 27.2 | 51.5 | 12.2 |
| 27.4 | 35.6 | 8.4 |
| 27.5 | 36.3 | 8.6 |
| 27.9 | 37.7 | 8.9 |
| 28.0 | 38.3 | 9.0 |

TABLE 6-continued

Compound 937 maleate salt, form II

| Position (Deg.) | Intensity (CPS) | Relative Intensity (%) |
|---|---|---|
| 28.2 | 30.6 | 7.2 |
| 28.4 | 19.0 | 4.5 |

TABLE 7

Compound 937 succinate salt, form I

| Position (Deg.) | Intensity (CPS) | Relative Intensity (%) |
|---|---|---|
| 5.2 | 1328.2 | 67.9 |
| 9.4 | 48.7 | 2.5 |
| 9.6 | 388.0 | 19.8 |
| 10.3 | 47.2 | 2.4 |
| 10.9 | 35.1 | 1.8 |
| 12.2 | 895.7 | 45.8 |
| 15.1 | 188.0 | 9.6 |
| 15.6 | 333.2 | 17.0 |
| 16.1 | 1956.0 | 100.0 |
| 17.0 | 270.5 | 13.8 |
| 17.6 | 437.5 | 22.4 |
| 18.7 | 123.8 | 6.3 |
| 19.2 | 148.8 | 7.6 |
| 19.9 | 33.2 | 1.7 |
| 20.4 | 151.2 | 7.7 |
| 21.5 | 41.2 | 2.1 |
| 21.9 | 431.6 | 22.1 |
| 22.9 | 1186.7 | 60.7 |
| 23.2 | 116.2 | 5.9 |
| 24.3 | 261.2 | 13.4 |
| 24.7 | 57.2 | 2.9 |
| 25.1 | 167.9 | 8.6 |
| 25.6 | 121.0 | 6.2 |
| 26.2 | 403.6 | 20.6 |
| 27.5 | 251.9 | 12.9 |
| 29.0 | 71.7 | 3.7 |
| 30.3 | 77.4 | 4.0 |
| 31.6 | 88.7 | 4.5 |
| 32.6 | 50.1 | 2.6 |
| 34.4 | 64.9 | 3.3 |
| 35.4 | 84.3 | 4.3 |
| 37.1 | 27.6 | 1.4 |

TABLE 8

Compound 937 succinate salt, form II

| Position (Deg.) | Intensity (CPS) | Relative Intensity (%) |
|---|---|---|
| 6.8 | 144.2 | 31.5 |
| 7.6 | 54.6 | 11.9 |
| 8.6 | 458.2 | 100.0 |
| 8.9 | 20.1 | 4.4 |
| 10.6 | 26.2 | 5.7 |
| 11.1 | 27.4 | 6.0 |
| 12.6 | 193.8 | 42.3 |
| 12.8 | 275.1 | 60.0 |
| 13.6 | 85.1 | 18.6 |
| 13.9 | 110.9 | 24.2 |
| 17.1 | 199.8 | 43.6 |
| 17.9 | 179.7 | 39.2 |
| 18.3 | 21.8 | 4.8 |
| 18.5 | 34.1 | 7.4 |
| 18.9 | 68.4 | 14.9 |
| 19.2 | 254.4 | 55.5 |
| 19.9 | 41.9 | 9.2 |
| 20.1 | 56.0 | 12.2 |
| 20.8 | 117.1 | 25.6 |
| 21.1 | 156.5 | 34.2 |

TABLE 8-continued

Compound 937 succinate salt, form II

| Position (Deg.) | Intensity (CPS) | Relative Intensity (%) |
|---|---|---|
| 21.4 | 203.0 | 44.3 |
| 22.3 | 101.0 | 22.0 |
| 22.5 | 50.5 | 11.0 |
| 22.8 | 97.1 | 21.2 |
| 23.9 | 66.3 | 14.5 |
| 24.3 | 154.9 | 33.8 |
| 24.8 | 128.2 | 28.0 |
| 25.5 | 19.9 | 4.3 |
| 25.7 | 57.1 | 12.5 |
| 25.9 | 61.8 | 13.5 |
| 26.6 | 34.1 | 7.4 |
| 27.3 | 52.3 | 11.4 |
| 28.8 | 20.2 | 4.4 |
| 29.2 | 67.8 | 14.8 |
| 29.4 | 64.7 | 14.1 |
| 29.7 | 20.6 | 4.5 |

TABLE 9

Compound 937 free base, form I

| Position (Deg.) | Intensity (CPS) | Relative Intensity (%) |
|---|---|---|
| 3.3 | 1055.2 | 89.7 |
| 6.6 | 967.3 | 82.2 |
| 9.1 | 170.5 | 14.5 |
| 9.5 | 504.7 | 42.9 |
| 9.9 | 257.3 | 21.9 |
| 11.1 | 299.5 | 25.4 |
| 12.2 | 281.3 | 23.9 |
| 13.3 | 48.1 | 4.1 |
| 16.0 | 280.0 | 23.8 |
| 17.4 | 267.7 | 22.7 |
| 18.0 | 128.0 | 10.9 |
| 18.2 | 72.9 | 6.2 |
| 18.9 | 89.7 | 7.6 |
| 19.1 | 17.3 | 1.5 |
| 19.4 | 31.9 | 2.7 |
| 19.9 | 47.8 | 4.1 |
| 20.1 | 20.6 | 1.8 |
| 20.4 | 67.0 | 5.7 |
| 21.0 | 57.0 | 4.8 |
| 21.4 | 310.2 | 26.4 |
| 22.9 | 31.7 | 2.7 |
| 23.5 | 140.6 | 11.9 |
| 24.5 | 1177.1 | 100.0 |
| 25.1 | 30.8 | 2.6 |
| 25.8 | 26.5 | 2.3 |
| 25.9 | 16.3 | 1.4 |
| 26.7 | 236.0 | 20.1 |
| 27.2 | 48.0 | 4.1 |
| 27.5 | 36.9 | 3.1 |
| 28.2 | 96.2 | 8.2 |

TABLE 10

Compound 937 fumarate salt, form II

| Position (Deg.) | Intensity (CPS) | Relative Intensity (%) |
|---|---|---|
| 4.1 | 109.9 | 21.4 |
| 5.3 | 124.9 | 24.3 |
| 5.8 | 83.6 | 16.3 |
| 6.8 | 54.9 | 10.7 |
| 8.4 | 45.9 | 9.0 |
| 9.0 | 29.8 | 5.8 |
| 9.2 | 70.2 | 13.7 |
| 11.2 | 26.3 | 5.1 |

TABLE 10-continued

Compound 937 fumarate salt, form II

| Position (Deg.) | Intensity (CPS) | Relative Intensity (%) |
| --- | --- | --- |
| 12.0 | 38.8 | 7.6 |
| 12.5 | 130.9 | 25.5 |
| 12.9 | 69.7 | 13.6 |
| 13.6 | 39.8 | 7.8 |
| 14.4 | 84.1 | 16.4 |
| 14.9 | 78.0 | 15.2 |
| 15.4 | 107.8 | 21.0 |
| 16.1 | 56.2 | 11.0 |
| 16.8 | 70.4 | 13.7 |
| 17.8 | 44.0 | 8.6 |
| 18.1 | 114.1 | 22.2 |
| 18.5 | 67.7 | 13.2 |
| 19.2 | 73.5 | 14.3 |
| 20.1 | 265.8 | 51.8 |
| 21.6 | 53.4 | 10.4 |
| 22.2 | 154.6 | 30.1 |
| 22.4 | 133.8 | 26.1 |
| 23.0 | 119.1 | 23.2 |
| 24.1 | 513.4 | 100.0 |
| 24.7 | 105.7 | 20.6 |
| 26.0 | 300.3 | 58.5 |
| 26.8 | 231.9 | 45.2 |
| 27.8 | 50.6 | 9.9 |
| 28.5 | 65.6 | 12.8 |
| 29.9 | 30.8 | 6.0 |

Example 7

Analytical Results by Means of Differential Scanning Calorimetry (DSC)

DSC analyses were carried out with a Perkin-Elmer DSC-7 apparatus. Aluminum DSC pans were loaded with about 2 mg of sample. The temperature range of the analyses was between 30° C. and a maximum value of 300° C. The samples were analyzed under nitrogen flow at a heating rate of 10° C./min.

FIG. 9 reports DSC thermograms of the salts and free base of compound 937 isolated at low scale as described in example 1.

FIG. 10 reports DSC thermograms of compound 937 salts isolated at higher scale as described in example 2 in comparison with the original free base and including profiles of known alternative crystalline forms.

In particular, DSC profiles 9A, 10A1, 11A and 11B1 are related to freebase form I while DSC profiles 10A2 and 11B2 relates to form II.

The DSC profile of a scaled-up batch of compound 937 fumarate salt form I, obtained according to example 3, is reported in FIG. 15. The observed melting endotherm with decomposition is at approximately 260° C. (peak temperature). It will be understood that the onset and/or peak temperature values of the DSC may vary slightly from one machine to another, one method to another or from one sample to another, and so the values quoted are not to be considered as absolute. In fact, observed temperatures will depend on the rate of temperature change as well as sample preparation technique and the particular instrument employed. It will be estimated and taken into account that the temperature values obtained applying such different conditions may vary by plus or minus about 4° C.

Example 8

Analytical Results by Means of Thermogravimetric Analysis (TGA)

TGA analyses were carried out with a Perkin-Elmer TGA-7 apparatus. Aluminum pans were loaded with 5÷10 mg of sample. The temperature range of the analyses was between 30° C. and a maximum value of about 250° C. The samples were analyzed under nitrogen flow at a heating rate of 2° C./min.

Example 9

Analytical Results by Means of Dynamic Vapour Sorption (DVS)

The water uptake of compound 937 salts and free base was investigated by submitting a sample of such substances to a hygroscopicity test by means of a DVS 1000 (SMS). The apparatus is a "controlled atmosphere microbalance" where the weighed sample is exposed to programmed variations of the relative humidity (RH) at a constant and controlled temperature. The measured parameters (weight, time and RH), reported in Excel worksheets, allow obtaining hygroscopicity curves over the tested RH range. Sorption/desorption cycles between 0% and 90% RH can be performed at controlled temperature of 25° C. Progressive variations of RH are of 10%; they are operated by the software at the equilibration of the sample weight. This condition can be defined at a constant rate of percent weight variation e.g. 0.005%/min. The experimental results are reported both as in the DVS Isotherm Reports and Isotherm Plots.

Examples of the DVS profiles of the compound 937 preferred salts, prepared as described in example 2, in comparison with the original free base are reported in FIG. 13.

An example of the water uptake of compound 937 fumarate salt during a DVS sorption ramp is here below summarized in the following table 11.

TABLE 11

Compound 937 fumarate salt DVS sorption data

| Relative Humidity (%) | Water uptake (%) |
| --- | --- |
| 0.0 | 0.0 |
| 10.0 | 0.1 |
| 20.0 | 0.3 |
| 30.0 | 0.4 |
| 40.0 | 0.6 |
| 50.0 | 0.9 |
| 60.0 | 1.2 |
| 70.0 | 1.4 |
| 80.0 | 1.5 |
| 90.0 | 1.6 |

Example 10

NMR Identification Analyses

The $^1$H NMR experiments were performed at a constant temperature of 28° C., on a Varian (nova 500 spectrometer operating at 499.8 MHz. A small amount of each sample was dissolved in 0.75 mL of DMSO-d6 and transferred into a 5-mm NMR tube for subsequent analysis. The analysis allows confirming the expected chemical structure of both molecule and counterions.

Example 11

Percent Compositions of a Formulation for Oral Use

| Ingredient | Range % |
|---|---|
| Compound 937 | 4-20 |
| Monohydrate Lactose | 45-55 |
| Pregelatinized Starch | 30-45 |
| Glyceryl Behenate | 1-2 |

Example 12

Powder Bulk Density

The determination of the powder bulk density of the fumarate, L-malate and L-tartrate salts of compound 937 and the freebase has been performed by manually filling hard gelatin capsules with the freely settled active ingredient.

The bulk density has been calculated by dividing the capsule filling weight consisting of the freely settled active ingredient by the known nominal volume of the hard gelatin capsule. The filling weight has been calculated as the difference between the gross weight of the filled capsule and the tare weight of the empty capsule.

The fumarate, L-malate and L-tartrate salts are characterized by powder bulk density values greater than 240 mg/ml while the density of the freebase is of about 90 mg/ml.

The person skilled in the art will appreciate from the above described data and examples that the new salts of compound 937 described in the invention are a new, improved and valuable tool in therapy.

The invention claimed is:

1. A salt of compound 937 wherein compound 937 has the formula:

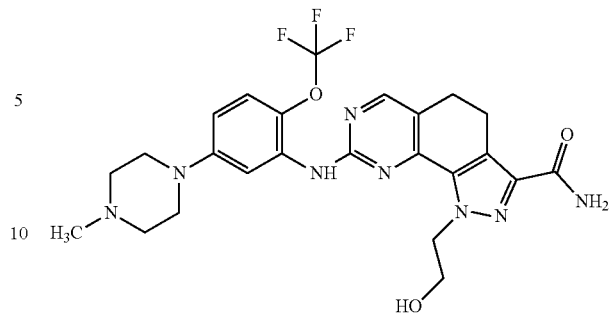

wherein the salt is selected from L-tartrate, succinate, phosphate, mesylate, maleate, L-malate, fumarate (half mole of counterion), fumarate, citrate (half mole of counterion), benzenesulfonate and L-aspartate (half mole of counterion), or a crystalline form, solvate, or hydrate thereof.

2. The salt of compound 937 as defined in claim 1, wherein the salt is selected from L-tartrate, succinate, maleate, L-malate and fumarate, or a crystalline form, solvate, or hydrate thereof.

3. The salt of compound 937 as defined in claim 1, wherein the salt is selected from L-tartrate, L-malate and fumarate, or a crystalline form, solvate, or hydrate thereof.

4. The crystalline form of the compound 937 fumarate salt of compound 937 as defined in claim 1, or a solvate, or hydrate thereof.

5. The crystalline form of the free base of compound 937 as defined claim 1.

6. A pharmaceutical composition comprising
   i) a salt of compound 937 as defined in claim 1;
   ii) a crystalline form of the fumarate salt of compound 937 as defined in claim 1; or
   iii) a crystalline form of the free base of compound 937 as defined in claim 1; and a pharmaceutically acceptable excipient and/or carrier.

7. A method for treating a mammal in need of PLK inhibition comprising administering to said mammal a therapeutically effective amount of
   i) a salt of compound 937 as defined in claim 1;
   ii) a crystalline form of the fumarate salt of compound 937 as defined in claim 1; or
   iii) a crystalline form of the free base of compound 937 as defined in claim 1.

* * * * *